US011904025B2

(12) United States Patent
Roy et al.

(10) Patent No.: US 11,904,025 B2
(45) Date of Patent: Feb. 20, 2024

(54) CYCLOPHANES FOR LIVE-CELL IMAGING

(71) Applicants: Northwestern University, Evanston, IL (US); King Abdulaziz City for Science and Technology (KACST), Riyadh (SA)

(72) Inventors: Indranil Roy, Chicago, IL (US); James Fraser Stoddart, Evanston, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 442 days.

(21) Appl. No.: 17/047,748

(22) PCT Filed: Apr. 16, 2019

(86) PCT No.: PCT/US2019/027713
§ 371 (c)(1),
(2) Date: Oct. 15, 2020

(87) PCT Pub. No.: WO2019/204329
PCT Pub. Date: Oct. 24, 2019

(65) Prior Publication Data
US 2021/0154331 A1    May 27, 2021

Related U.S. Application Data

(60) Provisional application No. 62/658,048, filed on Apr. 16, 2018.

(51) Int. Cl.
A61B 5/00 (2006.01)
A61B 8/00 (2006.01)
A61B 10/00 (2006.01)
A61K 49/00 (2006.01)

(52) U.S. Cl.
CPC ...... *A61K 49/0052* (2013.01); *A61K 49/0021* (2013.01)

(58) Field of Classification Search
CPC .................. A61K 49/0052; A61K 49/0021
See application file for complete search history.

(56) References Cited

U.S. PATENT DOCUMENTS 5,730,954 A    3/1998  Albayrak
2011/0104052 A1  5/2011  Barnett

OTHER PUBLICATIONS

Gong et al. (J. Am. Chem. Soc. 2017, 139, 4107-4116).*
Barnes et al. (J. Org. Chem. 2013, 78, 11962-11969).*
Shirinfar et al. (J. Am. Chem. Soc. 2012, 135, 90-93).*
Ziefle et al. (Arch Dermatol. 2010, 146, 843-847).*

Yapici, N. B., et al. "Highly stable and sensitive fluorescent probes (LysoProbes) for lysosomal labeling and tracking." Scientific reports 5 (2015): 8576-8576.
Yen, S. F., et al. "Interaction of aromatic imides with DNA. 1. Spectrophotometric and viscometric studies." Biochemistry 21.9 (1982): 2070-2076.
Young, R. M., et al. "Ultrafast conformational dynamics of electron transfer in exbox4+? perylene." The Journal of Physical Chemistry A 117.47 (2013): 12438-12448.
Zhang, J., et al. "Creating new fluorescent probes for cell biology." Nature reviews Molecular cell biology 3.12 (2002): 906-918.
Zheng, Q., et al. "Development of photostable fluorophores for molecular imaging." Current opinion in chemical biology 39 (2017): 32-38.
Zheng, Q., et al. "Ultra-stable organic fluorophores for single-molecule research." Chemical Society Reviews 43.4 (2014): 1044-1056.
Asakawa, M., et al. "Improved template-directed synthesis of cyclobis (paraquat-p-phenylene)." Journal of organic chemistry 61.26 (1996): 9591-9595.
Barnes, J. C., et al. "A radically configurable six-state compound." Science 339.6118 (2013): 429-433.
Barnes, J. C., et al. "ExBox: a polycyclic aromatic hydrocarbon scavenger." Journal of the American Chemical Society 135.1 (2013): 183-192.
Barnes, J. C., et al. "Synthesis of Ex n Box cyclophanes." The Journal of organic chemistry 78.23 (2013): 11962-11969.
Chen, X., et al. "Lysosomal Targeting with Stable and Sensitive Fluorescent Probes (Superior LysoProbes): Applications for Lysosome Labeling and Tracking during Apoptosis." Scientific Reports 5 (2015): 9004.
Coskun, A., et al. "High hopes: can molecular electronics realise its potential?." Chemical society reviews 41.14 (2012): 4827-4859.
Cunningham, C. W., et al. "Uptake, distribution and diffusivity of reactive fluorophores in cells: implications toward target identification." Molecular pharmaceutics 7.4 (2010): 1301-1310.
Dale, E. J., et al. "Supramolecular Explorations: Exhibiting the Ex tent of Ex tended cationic cyclophanes." Accounts of chemical research 49.2 (2016): 262-273.
Doupe, D. P., et al. "Visualizing and manipulating temporal signaling dynamics with fluorescence-based tools." Science signaling 7.319 (2014): re1-re1.
Dyar, S. M., et al. "Electron Transfer and Multi-Electron Accumulation in ExBox4+." Angewandte Chemie International Edition 53.21 (2014): 5371-5375.
Fernández-Suárez, M., et al. "Fluorescent probes for super-resolution imaging in living cells." Nature reviews Molecular cell biology 9.12 (2008): 929-943.
Gao, F.-P., et al. "Supramolecular adducts of squaraine and protein for noninvasive tumor imaging and photothermal therapy in vivo." Biomaterials 35.3 (2014): 1004-1014.
Gong, X., et al. "Intramolecular energy and electron transfer within a diazaperopyrenium-based cyclophane." Journal of the American Chemical Society 139.11 (2017): 4107-4116.
Grossi, M., et al. "Lysosome triggered near-infrared fluorescence imaging of cellular trafficking processes in real time." Nature Communications 7 (2016): 10855.

(Continued)

Primary Examiner — Michael G. Hartley
Assistant Examiner — Melissa J Perreira
(74) Attorney, Agent, or Firm — Quarles & Brady LLP

(57) ABSTRACT

Described herein are cyclophanes, compositions, and methods for live cell imaging. The cyclophanes comprise an ordered, cyclic arrangement of a chromophore, a first linker unit, a molecular strut, and a second linker unit. The compositions are capable of being taking up by cells and resist photobleaching under live-cell imaging conditions.

19 Claims, 16 Drawing Sheets

(56) References Cited

OTHER PUBLICATIONS

Guo, B., et al. "Decoration of porphyrin with tetraphenylethene: converting a fluorophore with aggregation-caused quenching to aggregation-induced emission enhancement." Journal of Materials Chemistry B 4.27 (2016): 4690-4695.
Haq, I. Reversible small molecule-nucleic acid interactions. In Nucleic Acids in Chemistry and Biology; Blackburn, G. M., Gait, M. J., Loakes, D., Williams, D. M., Eds.; the Royal Society of Chemistry: Cambridge, UK, 2006; pp. 341-382.
Hartlieb, K. J., et al. "Anticancer activity expressed by a library of 2, 9-diazaperopyrenium dications." ACS nano 9.2 (2015): 1461-1470.
Hendry, L. B., et al. "Small molecule intercalation with double stranded DNA: implications for normal gene regulation and for predicting the biological efficacy and genotoxicity of drugs and other chemicals." Mutation Research/Fundamental and Molecular Mechanisms of Mutagenesis 623.1-2 (2007): 53-71.
Hisamatsu, S., et al. "U-Shaped aromatic ureadicarboxylic acids as versatile building blocks: construction of ladder and zigzag networks and channels." Crystal growth & design 11.12 (2011): 5387-5395.
Hou, X., et al. "Tunable solid-state fluorescent materials for supramolecular encryption." Nature communications. 6 (2015): 6884.
Hyun, H., et al. "Central C—C bonding increases optical and chemical stability of NIR fluorophores." RSC advances 4.102 (2014): 58762-58768.
International Searching Authority. International Search Report and Written Opinion for application PCT/US2019/027713, dated Jul. 25, 2019. 11 pages.
Jensen, E. C. "Use of fluorescent probes: their effect on cell biology and limitations." The Anatomical Record: Advances in Integrative Anatomy and Evolutionary Biology 295.12 (2012): 2031-2036.
Jing, C., et al. "Chemical tags for labeling proteins inside living cells." Accounts of chemical research 44.9 (2011): 784-792.
Johnson, J. R., et al. "Thiazolothiazoles. I. The Reaction of Aromatic Aldehydes with Dithiooxamide1." Journal of the American Chemical Society 82.11 (1960): 2719-2724.
Juríček, M., et al. "Induced-fit catalysis of corannulene bowl-to-bowl inversion." Nature chemistry 6.3 (2014): 222-228.
Kaloyanova, S., et al. "Water-soluble NIR-absorbing rylene chromophores for selective staining of cellular organelles." Journal of the American Chemical Society 138.9 (2016): 2881-2884.
Kocaoglu, O et al. "Progress and prospects for small-molecule probes of bacterial imaging." Nature chemical biology 12.7 (2016): 472-478.
Larson, D. R., et al. "Water-soluble quantum dots for multiphoton fluorescence imaging in vivo." Science 300.5624 (2003): 1434-1436.
Lipke, M. C., et al. "Shuttling rates, electronic states, and hysteresis in a ring-in-ring rotaxane." ACS central science 4.3 (2018): 362-371.
Liu, Z., et al. "Imaging live-cell dynamics and structure at the single-molecule level." Molecular cell 58.4 (2015): 644-659.
Liu, Z., et al. "NLRP3 inflammasome activation is essential for paraquat-induced acute lung injury." Inflammation 38.1 (2015): 433-444.
Liu, Z., et al. "Surveying macrocyclic chemistry: from flexible crown ethers to rigid cyclophanes." Chemical Society Reviews 46.9 (2017): 2459-2478.
Long, L., et al. "A mitochondria-specific fluorescent probe for visualizing endogenous hydrogen cyanide fluctuations in neurons." Journal of the American Chemical Society 140.5 (2018): 1870-1875.
Lukinavicius, G., et al. "A near-infrared fluorophore for live-cell super-resolution microscopy of cellular proteins." Nature chemistry 5.2 (2013): 132-139.
Martineau, M., et al. "Semisynthetic Fluorescent pH Sensors for Imaging Exocytosis and Endocytosis." Nature communications 8.1 (2017): 1412.
Progatzky, F et al. "From seeing to believing: labelling strategies for in vivo cell-tracking experiments." Interface focus 3.3 (2013): 20130001.
Roy, B., et al. "A Pd8 tetrafacial molecular barrel as carrier for water insoluble fluorophore." Journal of the American Chemical Society 137.37 (2015): 11916-11919.
Roy, I., et al. "A multifunctional subphthalocyanine nanosphere for targeting, labeling, and killing of antibiotic-resistant bacteria." Angewandte Chemie International Edition 54.50 (2015): 15152-15155.
Shirinfar, B., et al. "Selective fluorescent detection of RNA in living cells by using imidazolium-based cyclophane." Journal of the American Chemical Society, vol. 135, No. 1, Dec. 21, 2012. Retrieved form the Internet: URL: https://pubs.acs.org/doi/10.1021/ja3112274. Abstract and Supporting Information.
Signore, G., et al. "Polarity-sensitive coumarins tailored to live cell imaging." Journal of the American Chemical Society 132.4 (2010): 1276-1288.
Stoddart, J. F. "Mechanically interlocked molecules (MIMs)—Molecular shuttles, switches, and machines (Nobel Lecture)." Angewandte Chemie International Edition 56.37 (2017): 11094-11125.
Suseela, Y. V., et al. "Imidazolyl-Naphthalenediimide-Based Threading Intercalators of DNA." ChemBioChem 17.22 (2016): 2162-2171.
Tong, C., et al. "Interaction of paraquat with calf thymus DNA: a terbium (III) luminescent probe and multispectral study." Journal of agricultural and food chemistry 58.9 (2010): 5257-5262.
Van Der Velde, Jhm, et al. "A simple and versatile design concept for fluorophore derivatives with intramolecular photostabilization." Nature Communications 7.10144: 1. 2016.
Wang, Y., et al. "Radically promoted formation of a molecular lasso." Chemical science 8.4 (2017): 2562-2568.
Wolfbeis, O. S. "An overview of nanoparticles commonly used in fluorescent bioimaging." Chemical Society Reviews 44.14 (2015): 4743-4768.
Woodward, A. N., et al. "Thiazolothiazole fluorophores exhibiting strong fluorescence and viologen-like reversible electrochromism." Journal of the American Chemical Society 139.25 (2017): 8467-8473.
Wu, Y., et al. "Probing distance dependent charge-transfer character in excimers of extended viologen cyclophanes using femtosecond vibrational spectroscopy." Journal of the American Chemical Society 139.40 (2017): 14265-14276.
Xie, J., et al. "Nanoparticle-based theranostic agents." Advanced drug delivery reviews 62.11 (2010): 1064-1079.

\* cited by examiner

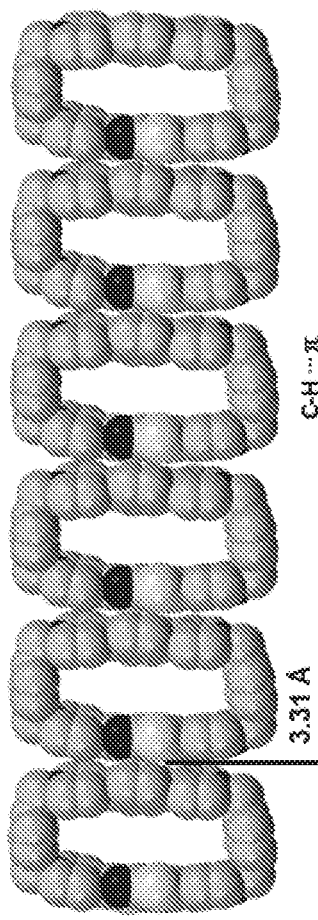
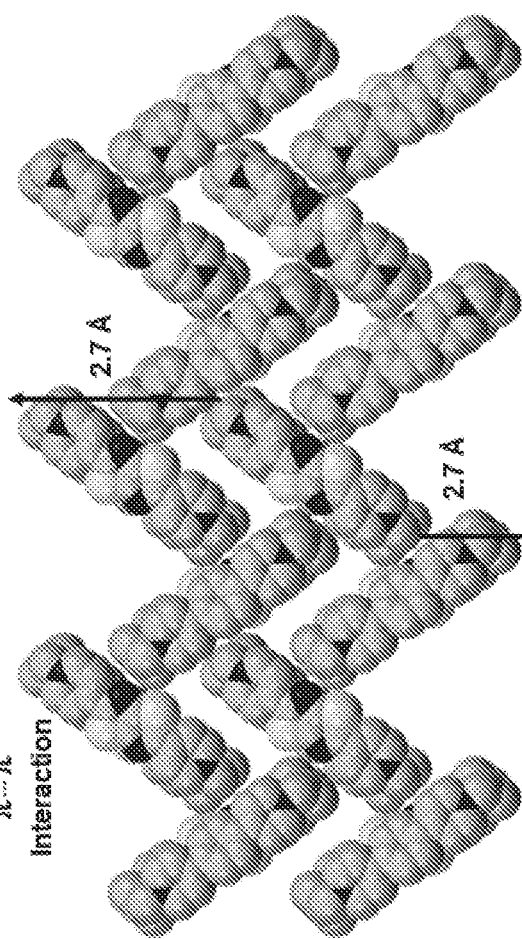
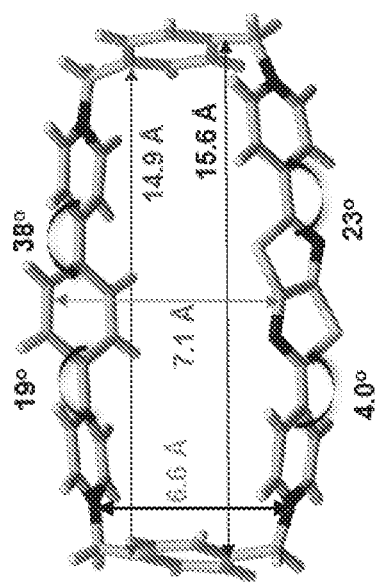
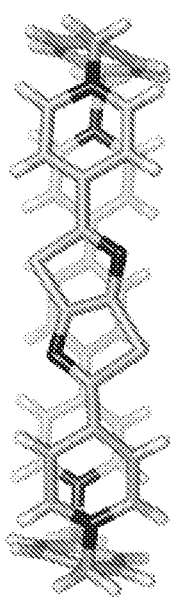
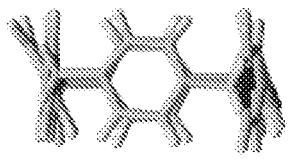
FIG 1A
FIG 1B
FIG 1C
FIG 1D
FIG 1E

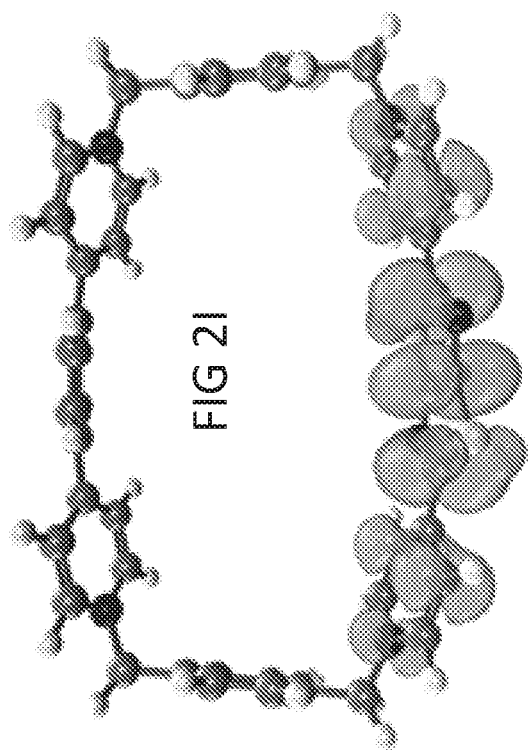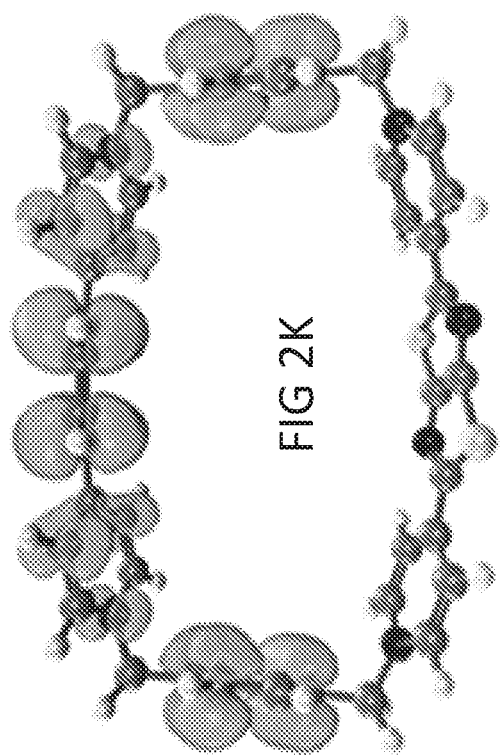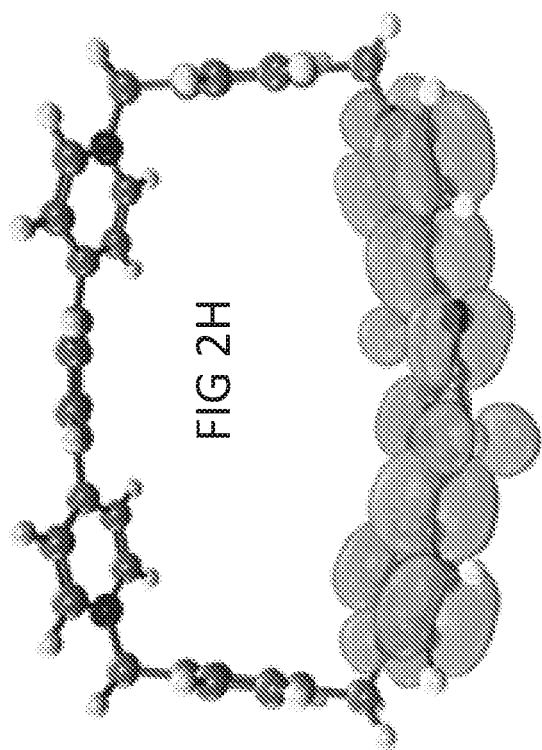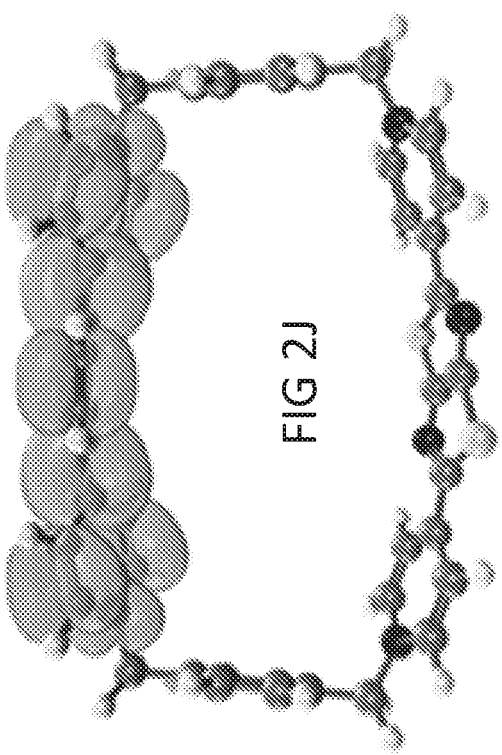

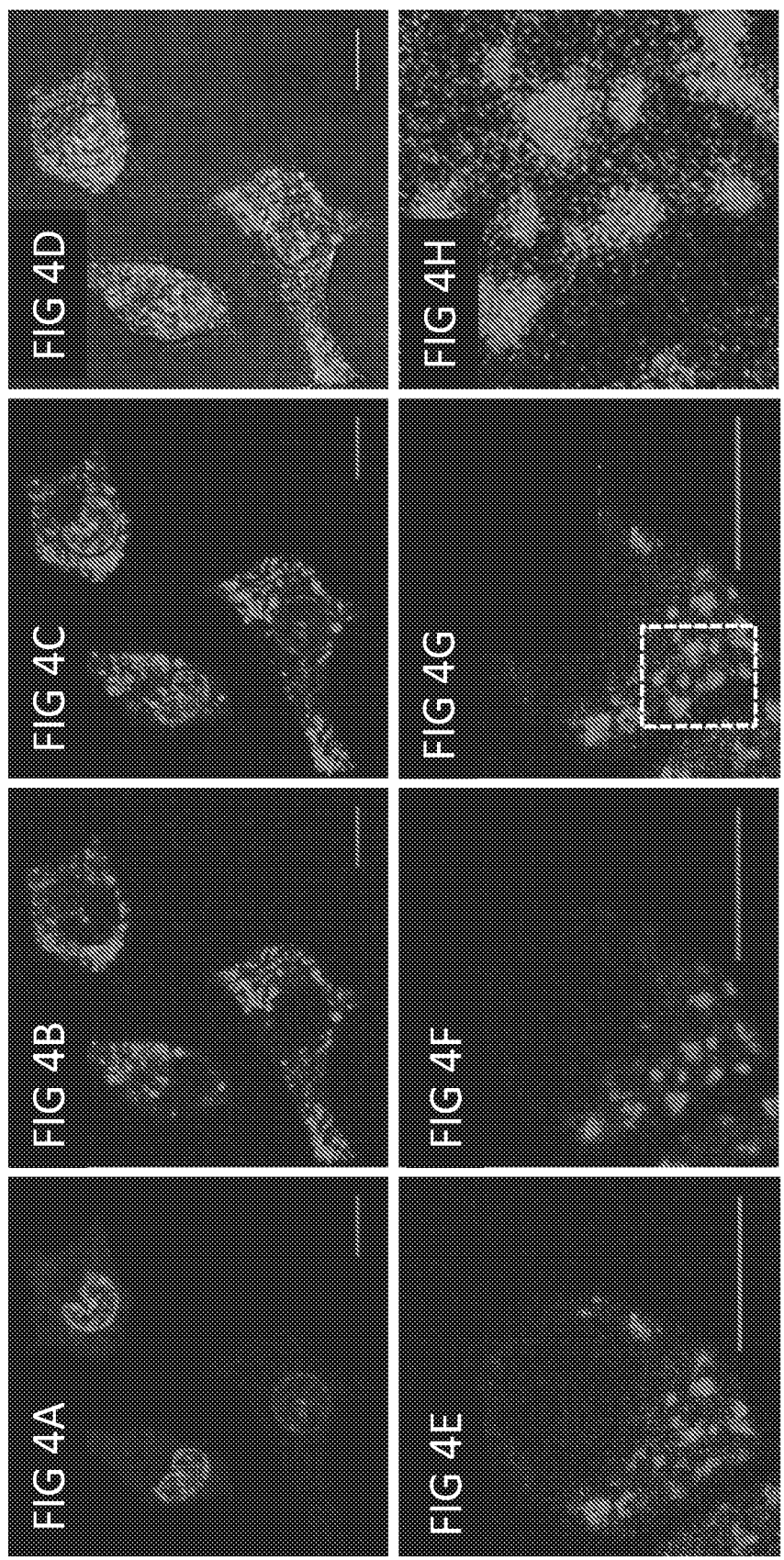

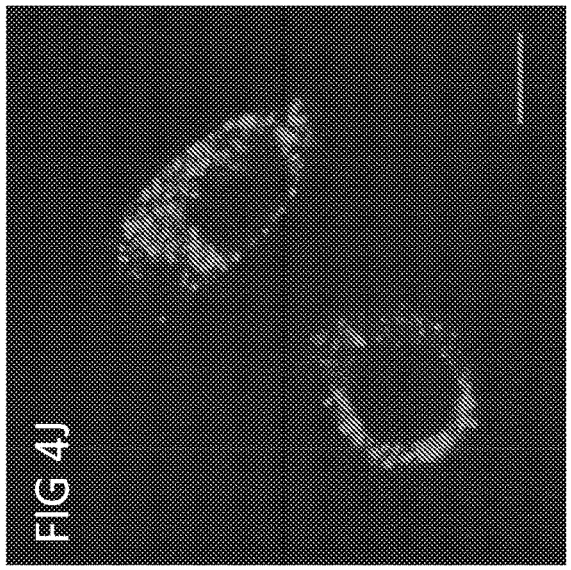
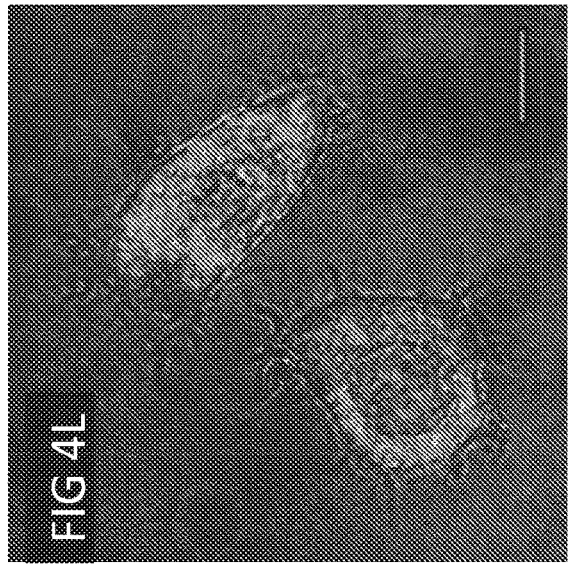
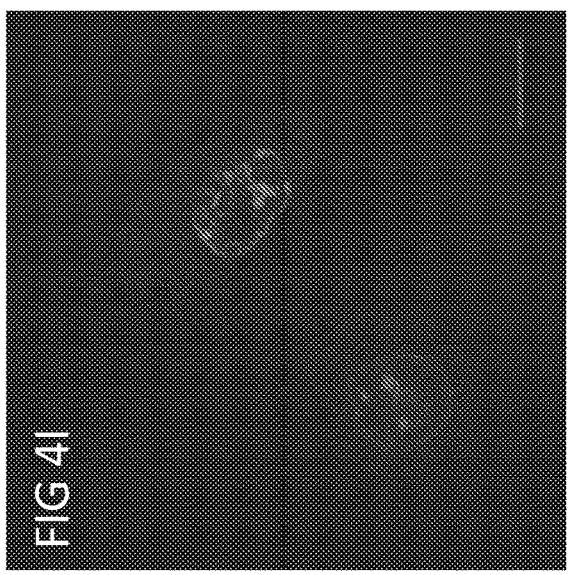
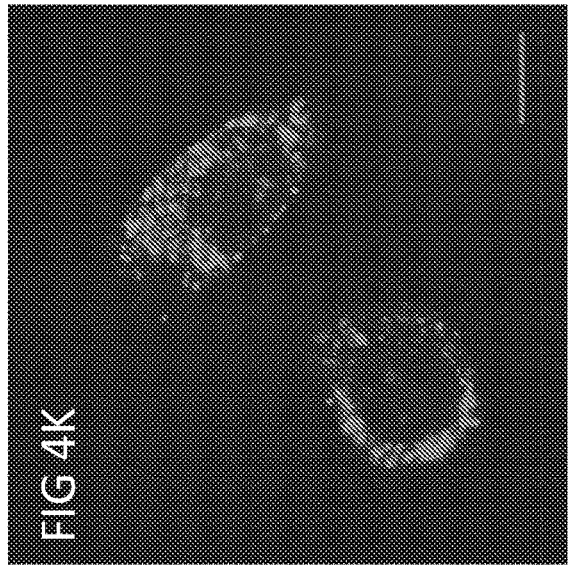

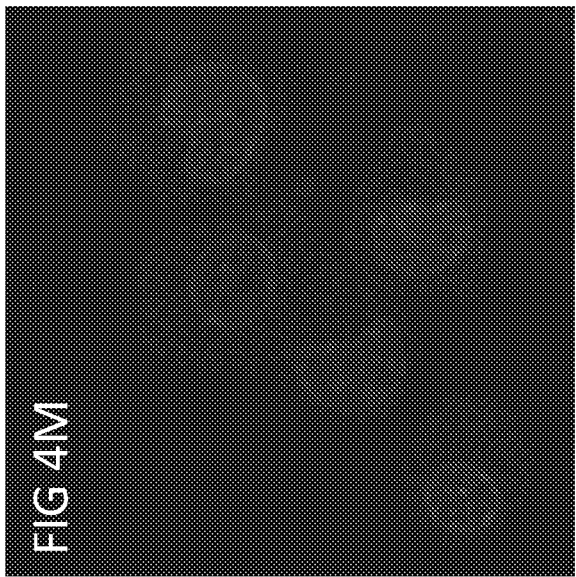
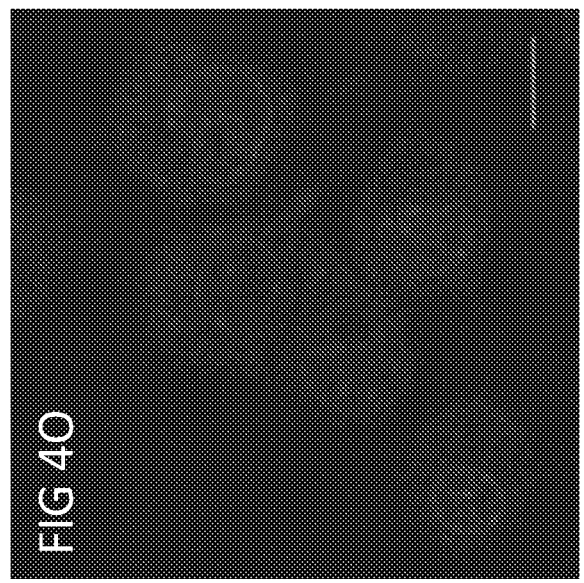
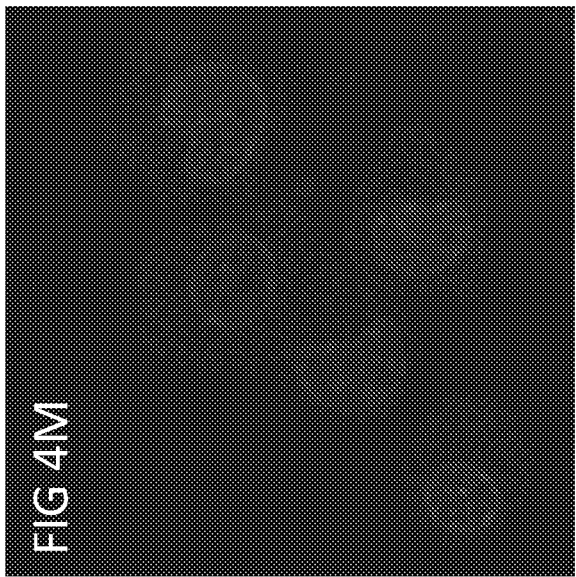
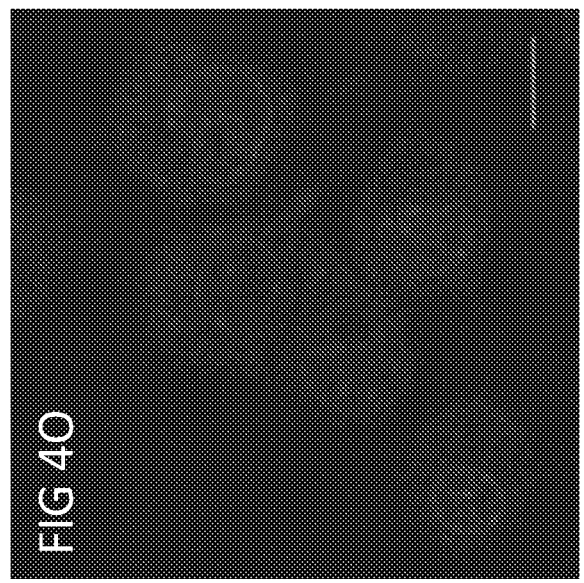

CYCLOPHANES FOR LIVE-CELL IMAGING

CROSS REFERENCE TO RELATED APPLICATIONS

The present application represents the U.S. national stage entry of International Application PCT/US2019/027713, filed Apr. 16, 2019, which claims benefit of priority to U.S. Provisional Application Ser. No. 62/658,048, filed Apr. 16, 2018, the contents of each are incorporated by reference in their entireties.

BACKGROUND

Live-cell imaging using probes has become an indispensable tool for medical diagnostics as well as for biological studies. This information, which allows us to follow the movement of intracellular proteins in living cells with extraordinary detail, is an essential tool for understanding how biological systems function. Fluorescent probes provide high sensitivity and great versatility, minimally perturbing the cells under investigation. Today, an expanded selection of probes, including organic dyes, metal-ligand complexes, polymer nanostructures and nanoparticles are available for use. Special attention is still required, however, in order to overcome, the common and the most important imaging-related issues, such as water solubility, pH sensitivity, photostability, membrane permeability, aggregation-induced quenching, and cell viability. The design and synthesis of new chromophores, having all of these properties, has proven to be challenging, and there exists a need for new fluorophores that can overcome these issues.

BRIEF SUMMARY OF THE INVENTION

Described herein are cyclophanes, compositions, and methods for live cell imaging. Cyclophanes for live-cell imaging comprise an ordered, cyclic arrangement of a chromophore, a first linker unit, a molecular strut, and a second linker unit. In some embodiments, the chromophore comprises a fluorescent thiazolothiazole unit; the molecular strut comprises a viologen unit; the first linker unit and the second linker unit each independently comprise a xylene linker; or any combination thereof. Suitably, the thiazolothiazole unit may comprise a dipyridyl thiazolothiazole and/or the molecular strut comprises an extended viologen. In some embodiments, wherein the cyclophane comprises a compound of Formula I

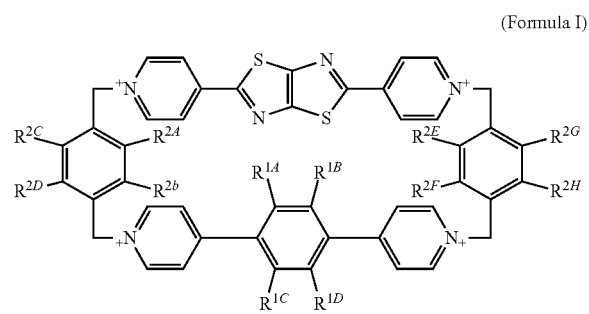

(Formula I)

wherein $R^{1A}$, $R^{1B}$, $R^{1C}$, $R^{1D}$, $R^{2A}$, $R^{2B}$, $R^{2C}$, $R^{2D}$, $R^{2E}$, $R^{2F}$, $R^{2G}$, and $R^{2H}$ are independently selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl.

Another aspect of the invention includes compositions comprises any of the cyclophanes described herein. In some embodiments, the composition comprises the cyclophane and a cytoplasmic delivery composition, a counterion, or both.

Another aspect of the invention includes crystalline compositions comprises any of the cyclophanes described herein.

Another aspect of the invention comprises methods for live-cell imaging. The method may comprise incubating cells with any of the cyclophanes described herein, stimulating the cyclophane with electromagnetic radiation, and detecting stimulated emission from the cyclophane. Suitably the cyclophane is simulated under live-cell conditions.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 1A-1E. Solid-state (super)structures of the ExTzBox$^{4+}$ obtained from single-crystal X-ray crystallography. (FIG. 1A) A stick representation showing the distances and the torsional angles associated with the box-like geometry. (FIG. 1B-1C) Stick representations of ExTzBox$^{4+}$ from a first side view (FIG. 1B) and a second side view (FIG. 1C). (FIG. 1D) Space-filling representation of a ExTzBox$^{4+}$ superstructure showing that the ExBIPY$^{2+}$ and TzBIPY$^{2+}$ units are facing each other. (FIG. 1E) Solid-state superstructure of ExTzBox$^{4+}$ revealing a zigzag arrangement.

(FIG. 2A) Absorption (maxima at 320 and 410 nm) and emission (maxima at 470) spectra of 6·4Cl in H$_2$O. (FIG. 2B) fsTA spectra of 6·4Cl in H$_2$O, 414 nm excitation. Downward arrow at the 505 nm maxima correspondence to 0.27, 0.87, 5.2, and 500 t/ps from top to bottom. (FIG. 2C) Cyclic voltammogram and DPV of 6$^{4+}$.

(FIG. 2D) Steady-state excitation (red line, $\lambda_{em}$=450 nm) and emission spectra (blue line, $\lambda_{em}$=380 nm) of 4·2Cl in H$_2$O at 295 K. (FIG. 2E) Fluorescence decay of 4·2Cl at 450 nm.

FIG. 2H-2K. Frontier orbitals of 6·4PF$_6$ showing both the HOMO and LUMO reside on TzBIPY moiety: (FIG. 2H) HOMO, (FIG. 2I) LUMO, (FIG. 2J) HOMO-1 and (FIG. 2K) LUMO+1.

(FIG. 2L) Cyclic voltammogram and (FIG. 2M) DPV of 4·2PF$_6$ in MeCN.

(FIG. 2N) Cyclic voltammogram and (FIG. 2O) DPV of 6·4PF$_6$ in MeCN.

(FIG. 3B) Calcein AM cell viability assay and (FIG. 3C) phototoxicity profiles of 6 under 25 mW excitation (410 nm).

FIG. 4A-4I1. Live-cell confocal microscopy images of RAW 264.7 macrophages cells. Cells were incubated with (FIG. 4A) SYTO nuclei, (FIG. 4B) 6·4Cl (20 µM in PBS solution). (FIG. 4C-4D) Composed images of the cells with red and blue channel. Cells were incubated with (FIG. 4E) LysoTracker green, (FIG. 4F) 6·4Cl (20 µM in PBS solution), (FIG. 4G) Composed images of the cells with green and blue channel, (FIG. 4H) zoom-in section of g showing the co-compartmentalization of 6·4Cl and LysoTracker green showing the presence of 6·4Cl into the lysosome of the living cells. Z-stacks of images were deconvolved using ImageJ package. Scale bar, 10 µm.

FIG. 4I-4L. Confocal fluorescence microscopy images of living raw blue macrophages cells. (FIG. 4I) Cells incubated with SYTO nuclei, (FIG. 4J) incubated with 6·4Cl (50 µM), (FIG. 4K-4L), composed images of cells. Z-stacks of images were deconvolved using ImageJ package. Scale bar, 10 µM.

FIG. 4M-4P. Confocal fluorescence microscopy images of living raw blue macrophages cells. (FIG. 4M) Cells incubated with SYTO nuclei, (FIG. 4N) incubated with reference 4·2Cl, (FIG. 4O-4P) composed images of cells. In comparison with 6·4Cl, the cells show much lesser fluorescence after incubation with reference. Z-stacks of images were deconvolved using ImageJ package. Scale bar, 10 µM.

(FIG. 6A) UV/Vis and (FIG. 6B) fluorescence spectra of 6·4Cl in 10% Fetal bovine serum. Inset: 6·4Cl in 10% Fetal bovine serum (10 µM) under 365 nm UV light.

DETAILED DESCRIPTION OF THE INVENTION

Figure 2A:
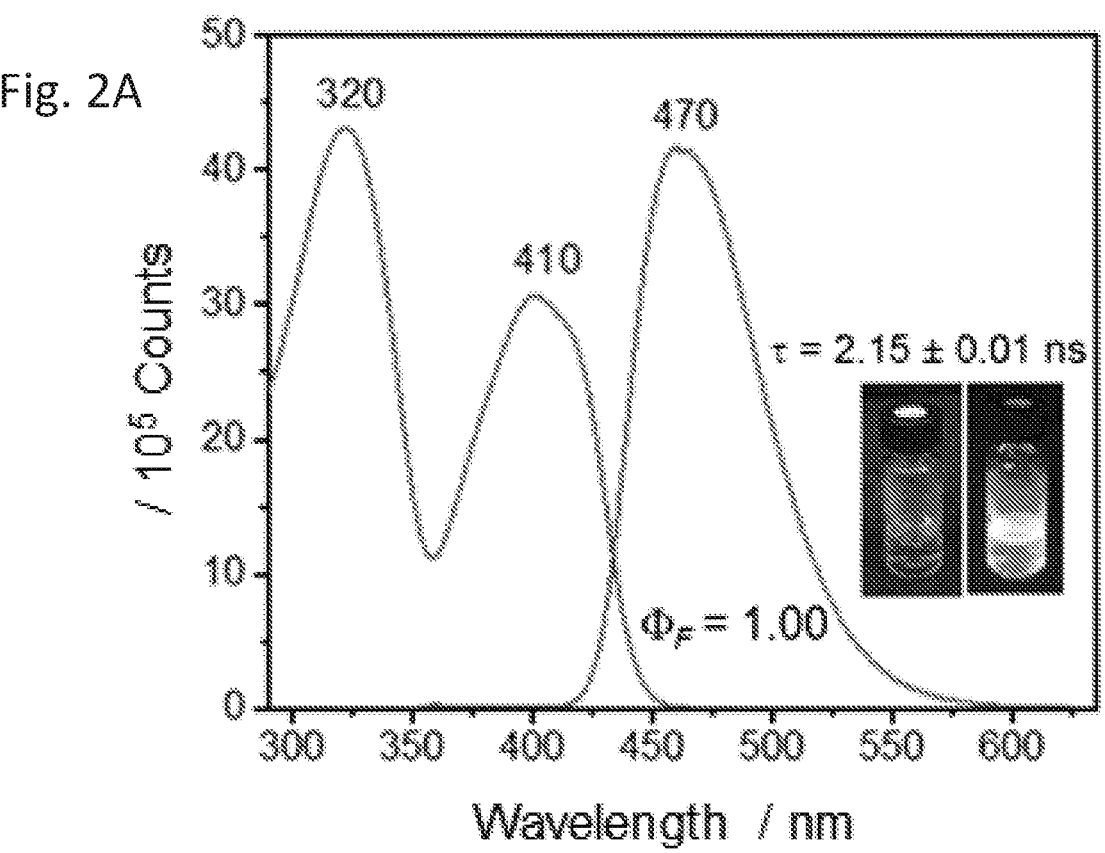
FIG. 2A-2C.

Described herein are compositions and methods for live cell imaging. The compositions are bright and persistent chromophores that resist photobleaching under live-cell imaging conditions. Moreover, these compositions are non-cytotoxic and can be delivered easily into the living cells. As a result, these composition have properties ideal for the use in live-cell imaging.

The compositions comprise a cyclophane having a chromophore incorporated therein. The cyclophanes disclosed herein are rigid and box-like as a result of the incorporation of a molecular strut into the cyclophane. Without wishing to be bound to theory, it is believe that the rigid, box-like structure prevents intercalation of the cyclophane into DNA or inhibits any other interactions that may be potentially cyctoxic to a host cell being imaged.

As demonstrated in the examples that follow, the compositions are capable of being taking up by cells and resist photobleaching under live-cell imaging conditions. Moreover the cyclophane comprising a fluorescent thiazolothiazole unit are resistant to photobleaching. In contrast, planar thiazolothiazoles that lack a rigid, box-like architecture readily photobleach in several seconds. As a result, these compositions described herein are useful for live-cell imaging and allow for persistent signals to be detected.

Cyclophanes may be prepared and their properties can be modified by changing their building units or introducing different functional groups into the cyclophanes by means of covalent bonds. Rigid, box-like cyclophanes may be less likely to intercalate into or interact electrostatically with DNA on account of their bulky structures, and hence may have low cytotoxicity. The cyclophanes described herein comprise a chromophore, a first linker unit, a molecular strut, and a second linker unit in an ordered, cyclic arrangement.

As used herein "chromophore" means a part of the cyclophane that may absorb electromagnetic radiation, suitably in the ultraviolet, visible, or infrared spectral region. The absorbed radiation may stimulate the cyclophane, exciting an electron from one molecular orbital to another higher energy molecular orbital, e.g., from the ground state to an excited state. In some cases, the absorption may be directly detectable. For example, the absorption may be detectable via an absorption or transmission spectroscopy. In other cases, the absorption is indirectly detectable. For example, the cyclophane may undergo a detectable relaxation event such as fluorescence.

In some embodiments, the chromophore is a fluorophore. As used herein "fluorophore" means a part of the cyclophane that may emit electromagnetic radiation as a result of the absorption of the electromagnetic radiation. Suitably the emitted radiation is red-shifted relative to the absorbed radiation. Suitably the emitted radiation may be in the ultraviolet, visible, or infrared spectral region. Fluorophores may comprise fused aromatic groups or a multiplicity of $\pi$-bonds in a substantially planar and/or cyclic portion of a molecule. Suitably the fluorophore comprises fused aromatic groups such as aryls or heteroaryls. Suitably the fluorophore is a fluorescent thiazolothiazole unit.

The thiazolothiazole unit may comprise any thiazolothiazole capable of being incorporated into the cyclophane and providing detectable simulated emission, such as fluorescence emission. In some embodiments, the thiazolothiazole unit comprises a dipyridyl thiazolothiazole. In particular embodiments, the thiazolothiazole unit comprises a

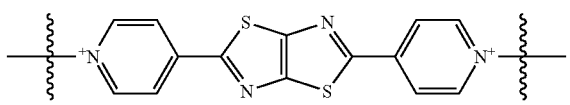 [SMILES: *[n+]1ccc(-c2nc3sc(-c4cc[n+](*)cc4)nc3s2)cc1]

diradical that is linked to the remainder of the cyclophane via the dipyridyl radical ends.

The cyclophane also comprises a molecular strut. As used herein, a "molecular strut" comprises a part of the cyclophane that provides stiffness or rigidity to the cyclophane. Suitably, the molecular strut resists large-amplitude confirmation rearrangement. The molecular strut may comprise a multiplicity of $\pi$-bonds in a substantially planar or linear arrangement. In some embodiments, the molecular strut comprises a multiplicity of aromatic groups. The multiplicity of aromatic groups may be covalently bonded vertex-to-vertex or fused together to provide stiffness and rigidity.

The molecular strut may comprise a viologen, suitably an extended viologen. Ignoring hydrogen or substituents, viologens may have a carbon-nitrogen backbone of —$(NC_5)(C_6)_n(C_5N)$—, where n is any suitable integer. In some embodiments, n is 0, 1, 2, 3, or more than 3. In some embodiments, n is equal to 1. The central aryl moiety, i.e, the bridging —$(C_6)_n$— diradical, may be substituted by one or more of the substituents at any of the carbon positions where hydrogen is present. In some embodiments, the extended viologen diradical may be represented by the formula

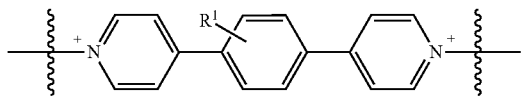

where the substituent $R^1$ may be recognized to be one or more substituents at any of the carbon positions where hydrogen is present. In certain embodiments, $R^1$ is selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl. In particular embodiments, $R^1$ is selected from the group consisting of hydrogen, a halogen, amino, a thiophene, and phenyl. As shown in the Examples below, a cyclophane comprising

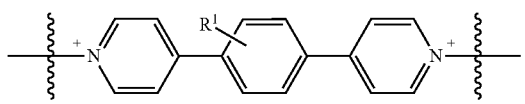

is capable of being taken up by living cells and providing persistent fluorescence emission.

The cyclophane composition may comprise linkers which are the same or different. Ignoring hydrogen or substituents, linkers may have a carbon backbone of $-(CH_2)_n(C_6)_o(CH_2)_m-$, where n, m and o are any suitable integer. In some embodiments, n and/or m is 1, 2, 3, or more than 3. In some embodiments, o is 1, 2 or 3. In some embodiments, n, m, and o are each 1. The central aryl moiety, i.e, the bridging $-(C_6)_o-$ diradical, may be substituted by one or more substituents at any of the carbon positions where hydrogen is present. In some embodiments, the linkers may be represented by the formula

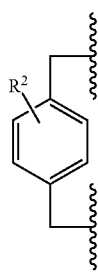

where the substituent $R^2$ may be recognized to be one or more substituents at any of the carbon positions where hydrogen is present. In certain embodiments, $R^2$ is selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl. In particular embodiments, $R^2$ is selected from the group consisting of hydrogen, a halogen, amino, thiophene, and phenyl. As shown in the Examples below, a cyclophane comprising

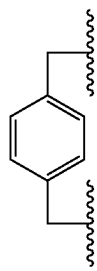

linkers is capable of being taken up by living cells and providing persistent fluorescence emission.

In some embodiments, the composition comprises a compound of Formula I

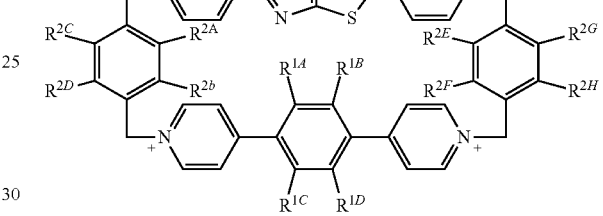

(Formula I)

wherein $R^{1A}$, $R^{1B}$, $R^{1C}$, $R^{1D}$, $R^{2A}$, $R^{2B}$, $R^{2C}$, $R^{2D}$, $R^{2E}$, $R^{2F}$, $R^{2G}$, and $R^{2H}$ are independently selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl. In certain embodiments, $R^{1A}$, $R^{1B}$, $R^{1C}$, $R^{1D}$, $R^{2A}$, $R^{2B}$, $R^{2C}$, $R^{2D}$, $R^{2E}$, $R^{2F}$, $R^{2G}$, and $R^{21H}$ are independently selected from the group consisting of hydrogen, a halogen, amino, a thiophene, and phenyl. In a particular embodiment, the composition comprises a compound of a compound of Formula Ia

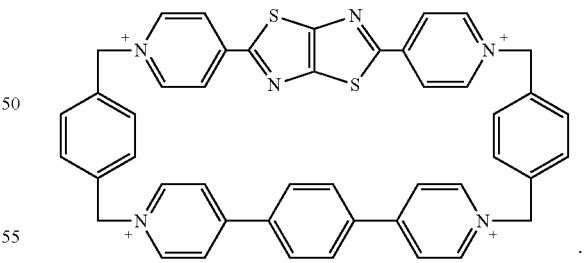

(Formula Ia)

Compositions comprising the cyclophanes described herein may be prepared. The composition may further comprise one or more cytoplasmic delivery compositions and/or a counterion. The cytoplasmic delivery composition may be selected from a liposome, a synthetic polymer, a cell-penetrating peptide, a nanoparticle, a viral particle, an electroporation buffer, a nucleofection reagent, or any combination thereof. Suitably the counterion is an anion such as a halide or $PF_6^-$. In some embodiments, the composition is a crystalline composition comprising any of the cyclophanes described herein. Suitably the crystalline composition may comprises a counterion such as an anion.

Cyclophanes as described above may be synthesized without the use of a template as illustrated in Scheme I. 2,5-di(pyridin-4-yl)thiazolo[5,4-d]thiazole (TzBIPY, III) may be reacted with V·2PF$_6$ in 1:1 ratio in dry MeCN and in the presence of ~5 mol % "Bu$_4$NI under refluxing conditions was followed by the addition of solid "Bu$_4$NCl to precipitate a crude product that may be washed with CH$_2$Cl$_2$ and dissolved in H$_2$O. Counterion exchange (NH$_4$PF$_6$) produces a precipitate, which can filtered and subjected to reverse-phase column chromatography, affording VI·4PF$_6$. Any exemplary synthesis preparing the compound of Formula I is provided below.

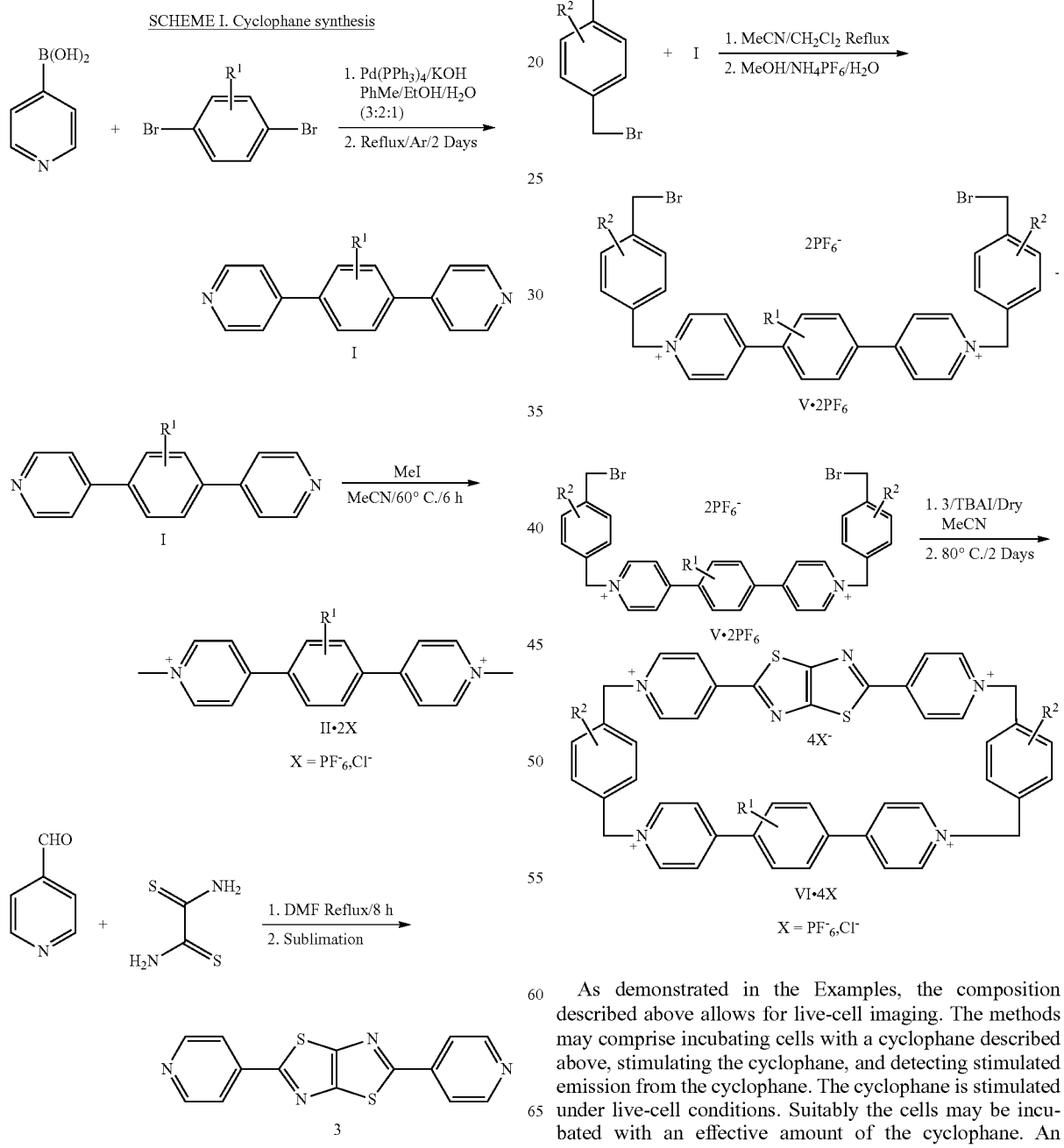

As demonstrated in the Examples, the composition described above allows for live-cell imaging. The methods may comprise incubating cells with a cyclophane described above, stimulating the cyclophane, and detecting stimulated emission from the cyclophane. The cyclophane is stimulated under live-cell conditions. Suitably the cells may be incubated with an effective amount of the cyclophane. An effective amount of the cyclophane is an amount of the cyclophane capable of producing a detectable signal after having transfected across a cellular membrane or was otherwise taken up by a cell. Suitably the cyclophance is capable of producing a detectable signal under live-cell conditions. Because the cyclophanes are non-cytotoxic, the cells may be incubated by an effective amount of the cyclophane without substantial decrease in cell viability. Cell viability may be determined by any suitable technique such as with the use of an MTT assay. As used herein, "substantial decrease in cell viability" means viability of incubated cells less than 80% over a period of at least an hour. Suitably, cell viability may be at least 80%, 85%, 90%, 91%, 92%, 93%, 94%, 95%, 96%, 97%, 98%, or 99% over a period of 1, 2, 4, 6, 8, 12, or 24 hours. The cyclophanes described herein allow for persistent detection over extended period of time without photobleaching. Suitably the cyclophanes may be detected over periods of at least 5 seconds. Suitably, the cyclophanes may be detected over periods of at least 1 minute, 5 minutes, 10 minutes, 15 minutes, 30 minutes, 45 minutes, or 60 minutes without substantial loss in intensity. A substantial loss of intensity occurs when the detectable signal is less than half the intensity at the time of measurement than at the initiation of irradiation. Suitably, the cyclophanes may have a detectable intensity of at least 50%, 60%, 70%, 80%, or 90% for at least 1 minute, 5 minutes, 10 minutes, 15 minutes, 30 minutes, 45 minutes, or 60 minutes after the initiation of irradiation. The stimulated emission may be fluorescence emission detectable in the ultraviolet, visible, or infrared spectral region and detected by methods known in the art such as fluorescence microscopy. The cyclophane may be stimulated by ultraviolet or visible radiation.

Live-Cell Imaging

The ideal fluorescent probe for live-cell imaging is bright, non-cytotoxic, and can be delivered easily into the living cells in an efficient manner. The design of synthetic fluorophores, having all three of these properties, however, has proved to be challenging. Here, we introduce an effective strategy for designing a new class of fluorescent probes for live-cell imaging. A box-like hybrid cyclophane, namely ExTzBox·4X (6·4X, X=$PF_6^-$, $Cl^-$), has been synthesized by connecting an extended viologen (ExBIPY) molecular strut and a dipyridyl thiazolothiazole (TzBIPY) chromophore in an end-to-end fashion with two p-xylylene (p-Xy) linkers. Photophysical studies show that 6·4Cl has a quantum yield, $\Phi_F$=1.00. Furthermore, unlike its $ExBIPY^{2+}$ and $TzBIPY^{2+}$ building units, 6·4Cl is non-cytotoxic to RAW 264.7 macrophages, even with a loading concentration as high as 100 μM. It is believed that the rigid box-like structure prevents intercalation into DNA or inhibits any other interactions with it.

Confocal microscopy has demonstrated that $6^{4+}$ is taken up by the RAW 264.7 macrophages, allowing the cells to glow brightly with blue laser excitation, without any hint of photobleaching or disruption of normal cell behavior under the imaging conditions. By contrast, the acyclic reference compound $Me_2TzBIPY·2Cl$ (4.2·Cl) shows very little fluorescence, inside the cells, which is quenched completely under the same imaging conditions. The in vitro cell investigations underscore the significance of using highly fluorescent box-like rigid cyclophanes for live-cell imaging. $Me_2TzBIPY·2Cl$ (4.2·Cl) as well as ExBox·4Cl (7.2Cl), BlueBox·4Cl (8.2·Cl), $Me_2ExBIPY·2Cl$ (2·2Cl), and paraquat·2Cl (9.2Cl) are illustrated below.

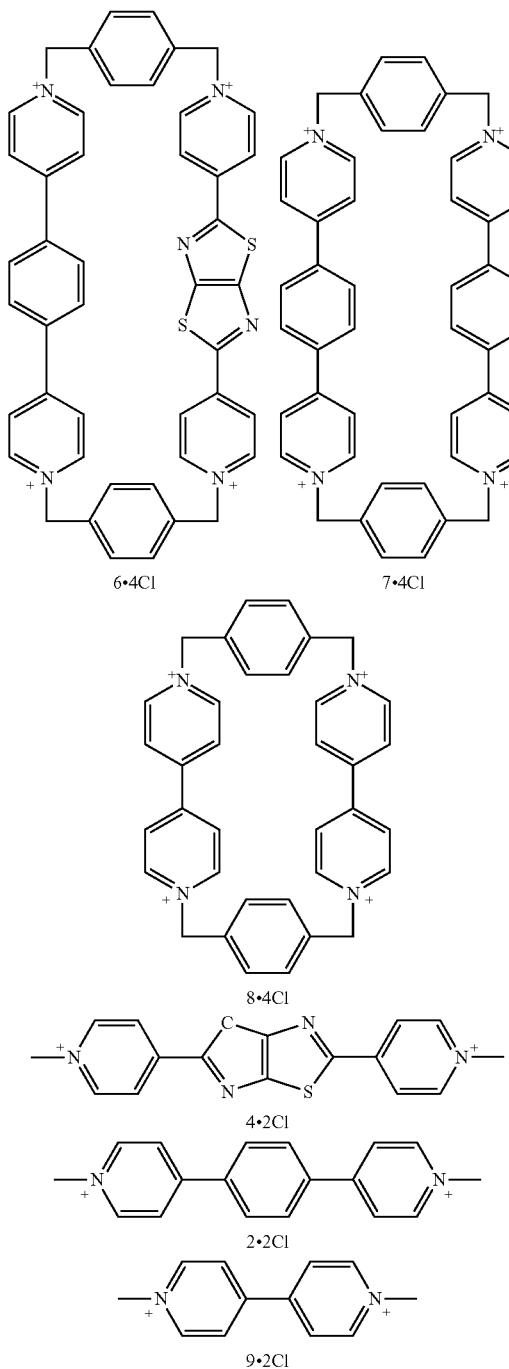

In order to understand their potential as imaging agents, it is necessary to (i) establish their toxicity profiles, (ii) demonstrate their cellular uptake and (iii) delineate the cells at least in vitro. We incorporated a fluorophore in between two bipyridinium units to produce a fluorescent cyclophane that may be used for live-cell imaging. We selected thiazolothiazole as the fluorophore since it possesses excellent photophysical properties and may be incorporated synthetically between the bipyridinium units. In order to match its length, we opted to incorporate a molecular strut comprising an extended bipyridinium unit on the other side of the cyclophane.

Here, we report the rational design and synthesis of a rigid, box-like hybrid cyclophane, ExTzBox·4X (6·4X, X=$PF_6^-$, $Cl^-$), containing one ExBIPY (1) unit and one TzBIPY (3) unit, which are bridged together by two para-xylylene (p-Xy) linkers. This constitutionally asymmetric tetracationic cyclophane is readily soluble in both polar organic solvents, e.g., McCN, $Me_2CO$, and DMF as its $PF_6^-$ salt, and in $H_2O$ as either its $Cl^-$ or $TFA^-$ salt. Combined steady-state and time-resolved experiments were carried out in order to investigate the photophysical processes of 6·4Cl. 3-(4,5-Dimethylthiazol-2-yl)-2,5-diphenyltetrazolium bromide (MTT) assays were performed so as to understand toxicity profiles of 6·4Cl and its building units in the reference salts, $Me_2$ExBIPY·2Cl (2·2Cl) and $Me_2$TzBIPY·2Cl (4.2·Cl). Finally, 6·4Cl was employed for live-cell imaging. Our investigations demonstrate that $6^{4+}$ enters the lysosomes of living macrophages, allowing the cells to glow brightly under irradiation of blue laser light.

The hybrid cyclophane, ExTzBox·4X (6·4X, X=$PF_6^-$, $Cl^-$) was synthesized (Scheme 1) without the use of a template. In a typical experiment, the reaction of 2,5-di(pyridin-4-yl)thiazolo[5,4-d]thiazole (TzBIPY, 3) and DB·2$PF_6$(5·2$PF_6$) in 1:1 ratio in dry MeCN and in the presence of ~5 mol % $^nBu_4NI$ under refluxing conditions was followed by the addition of solid $^nBu_4NCl$ to precipitate the crude product, which was washed with $CH_2Cl_2$ and dissolved in $H_2O$. Counterion exchange ($NH_4PF_6$) produced a precipitate, which was filtered and subjected to reverse-phase column chromatography, affording 6·4$PF_6$ in 25% yield based on 5·2$PF_6$. A combination of $^1H$ and $^{13}C$ nuclear magnetic resonance (NMR) spectroscopy and high-resolution mass spectrometry (HRMS) confirmed the formation of 6·4$PF_6$. Water soluble 6·4Cl was obtained from 6·4$PF_6$, following counterion exchange ($^nBu_4NCl$/MeCN).

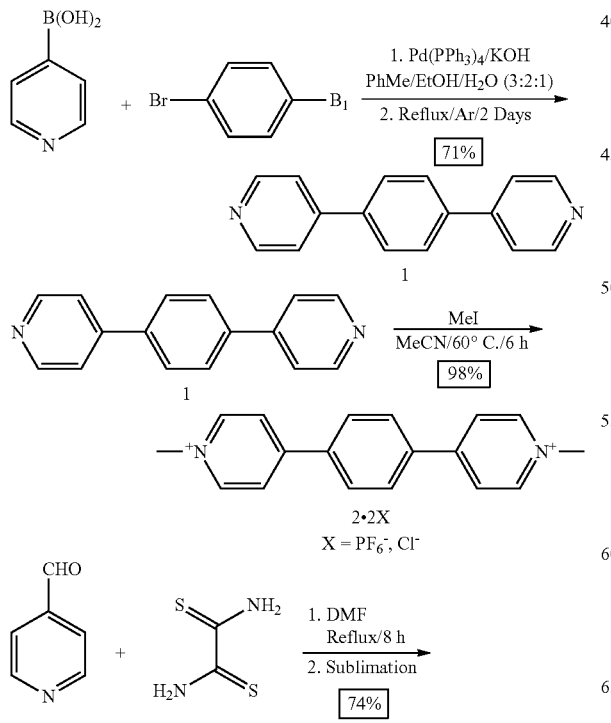

SCHEME 1. Synthesis of ExTzBox·4X

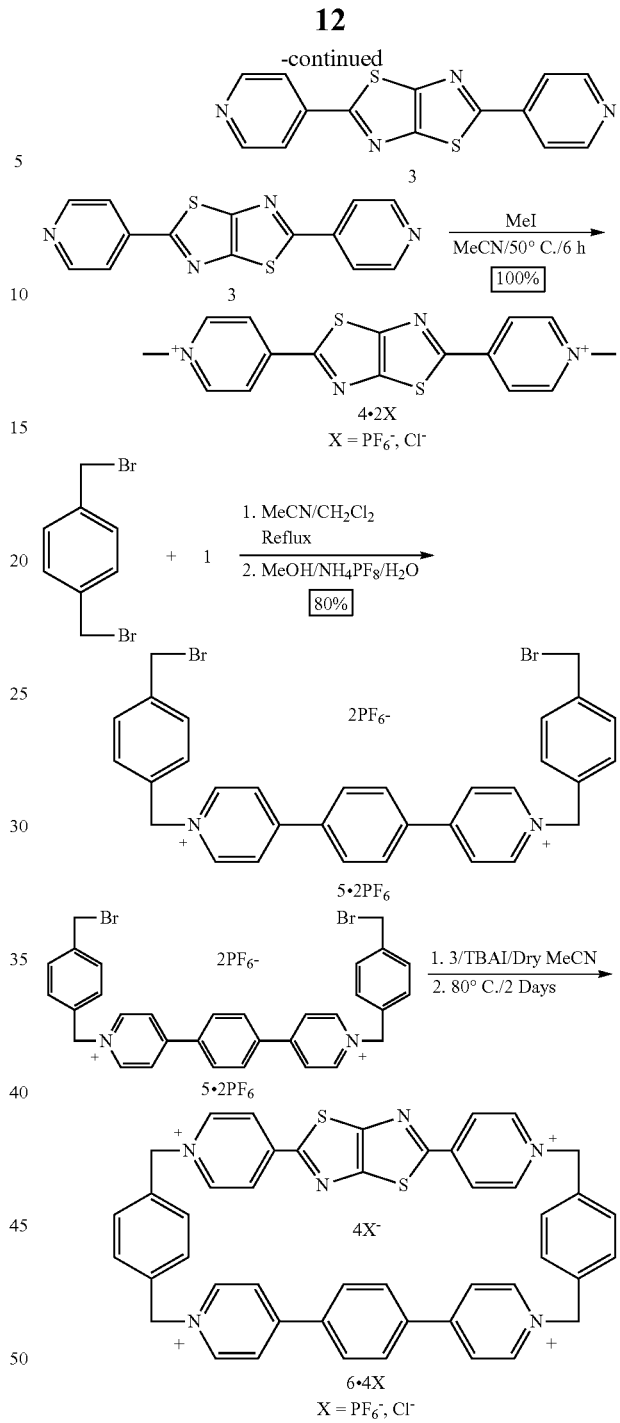

Further evidence for cyclophane formation comes from single-crystal X-ray diffraction (XRD) analysis. Single crystals were grown by vapor diffusion of i-$Pr_2O$ into a MeCN solution of 6·4$PF_6$ for 3-4 days. The solid-state (super) structure reveals (FIG. 1A-1E) a box-like cyclophane for $6^{4+}$ measuring 15.6 Å in length, and 6.6 and 7.1 Å in width at its periphery and center, respectively. The two torsional angles between the pyridinium and phenylene rings associated with the ExBIPY$^{2+}$ unit are 19° and 38°. The two torsional angles between the pyridinium and thiazolothiazole rings, however, at the TzBIPY$^{2+}$ unit are 4° and 23°. This flatter conformation for the TzBIPY$^{2+}$ unit in $6^{4+}$ is presumably a result of the absence of H atoms on the thiazolothiazole unit and its planar fused-ring geometry. The extended solid-state superstructure of $6^{4+}$ reveals that ExBIPY$^{2+}$ and TzBIPY$^{2+}$ units are facing each other with a short intermolecular π . . . π distance of 3.31 Å from the centroid of TzBIPY$^{2+}$ to the phenylene ring in ExBIPY$^{2+}$. C—H . . . π Interactions are observed between the p-Xy rings and the adjacent cyclophanes (C—H . . . π distance of 2.7 Å). The overall superstructure of $6^{4+}$ reveals (FIG. 1E) a zigzag arrangement of the cyclophanes.

The steady-state absorption and emission spectra of 6·4Cl in H$_2$O are shown in FIG. 2A. The absorption spectrum of 6·4Cl exhibits absorbance maxima in its UV region at $\lambda_{max}$=320 nm and in its visible region at $\lambda_{max}$=410 nm, both bands being characteristic of ExBIPY$^{2+}$ and TzBIPY$^{2+}$ units, respectively. The absorption spectrum of the reference Me$_2$TzBIPY$^{2+}$ ($4^{2+}$), is similar to that of $6^{4+}$ except that it has a lower molar extinction coefficient and a slightly blue-shifted absorption maximum (FIG. 2D-2E), suggesting that, photophysically, the thiazolothiazole unit in $6^{4+}$ behaves as a reference monomer. The cyclophane $6^{4+}$ shows bright blue fluorescence in H$_2$O and possesses an emission maximum at $\lambda_{max}$=470 nm with a fluorescence quantum yield of unity. The cyclophane $6^{4+}$ is extremely photostable and retains its photophysical properties in H$_2$O for several months under natural daylight. In order to assess the photostability of $6^{4+}$, photobleaching studies were performed under UV flashlight (18 W, 395 nm), and the results were compared with those of a commercially available nucleic acid staining dye, Hoechst 33258. The experimental results (FIG. 5A-5B) show a little loss of absorbance intensity of $6^{4+}$ after 60 min of UV light irradiation, which is comparable to the photo-stability of Hoechst dye. It also endures strong acidic conditions (pH=1) and operates in a broad pH range (pH=1 to 7) without any change (FIG. 2F-2G) of its fluorescence characteristics. Furthermore, the fluorescence spectrum of $6^{4+}$ in serum is similar to the spectrum obtained in water, with slightly lower fluorescence intensity (FIG. 6A-6B), indicating little influence of serum proteins on the fluorescence emission of $6^{4+}$.

Figure 2B:
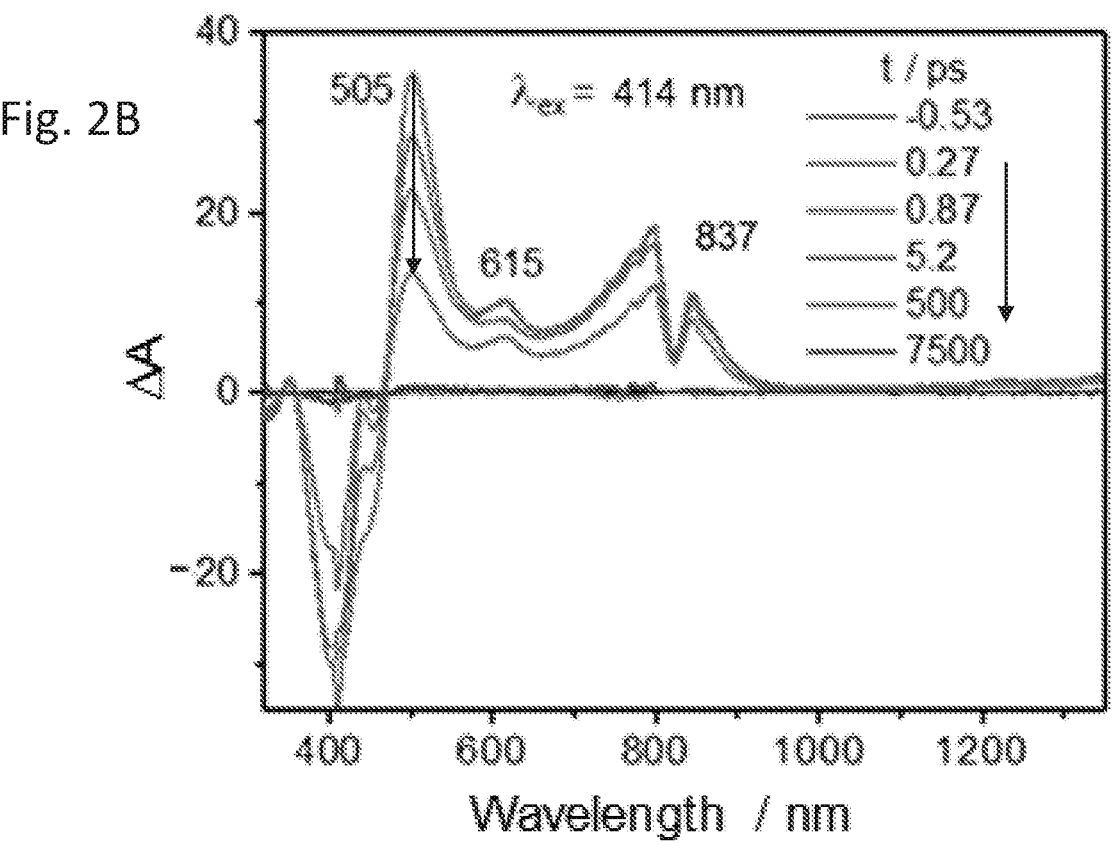
Figure 2C:
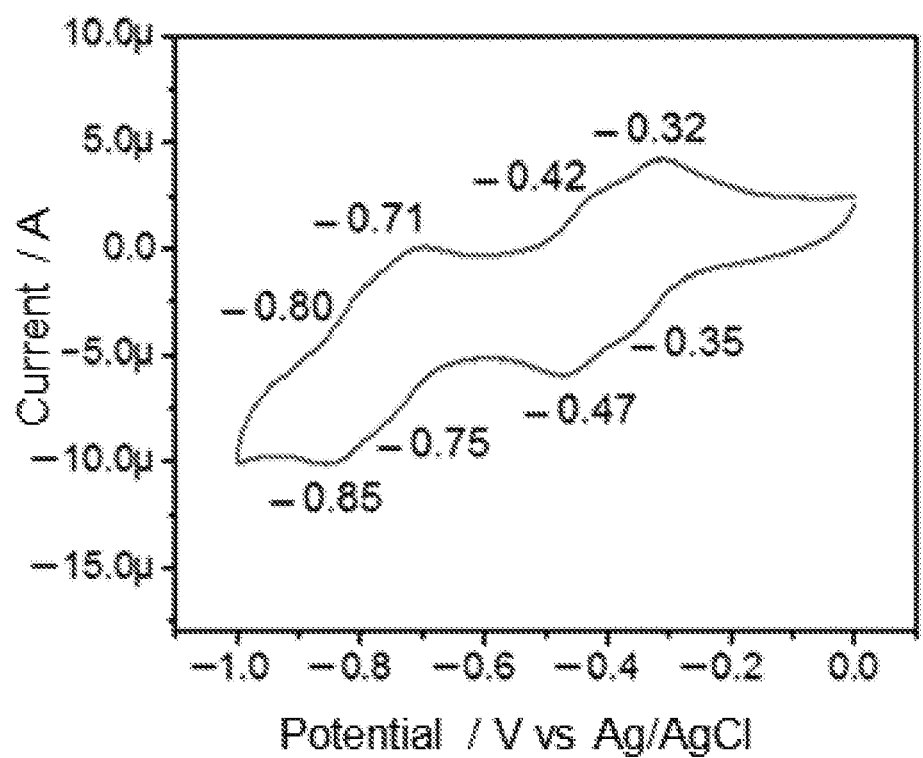
Figure 2D:
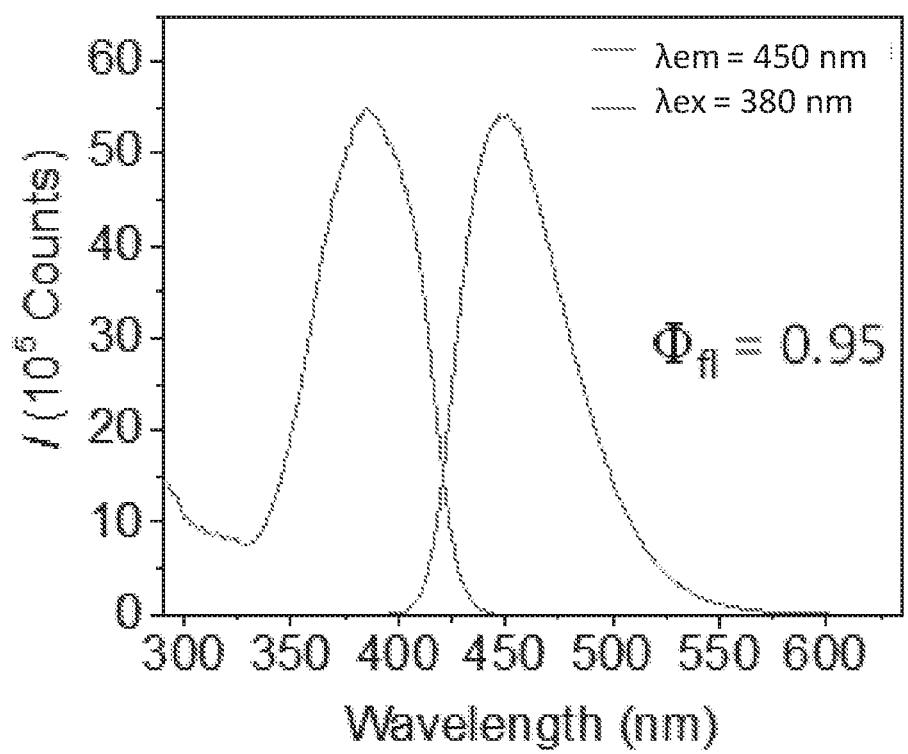
FIG. 2D-2E.
Figure 2E:
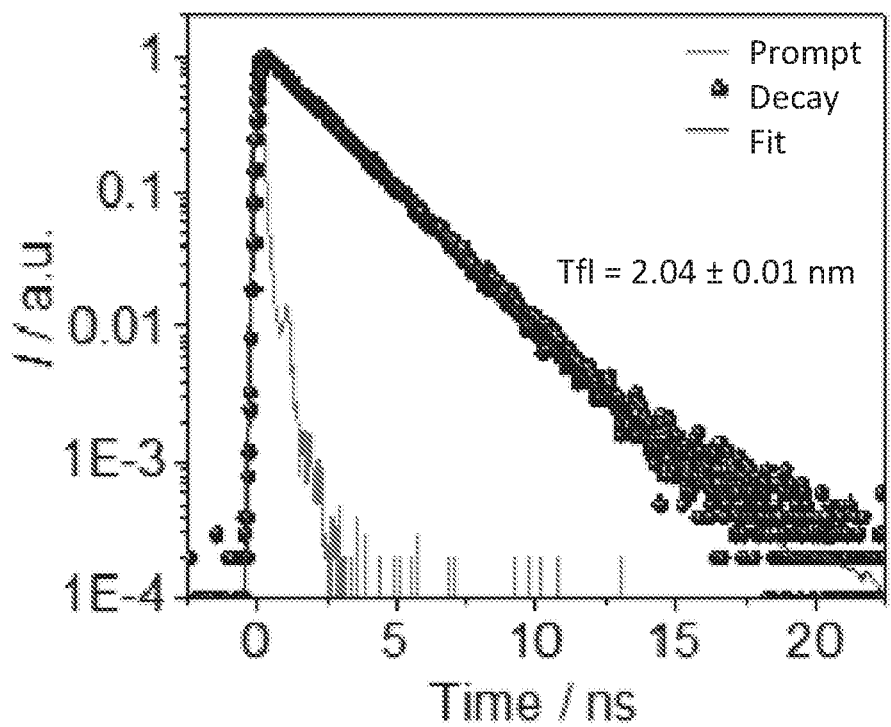
Figure 2F:
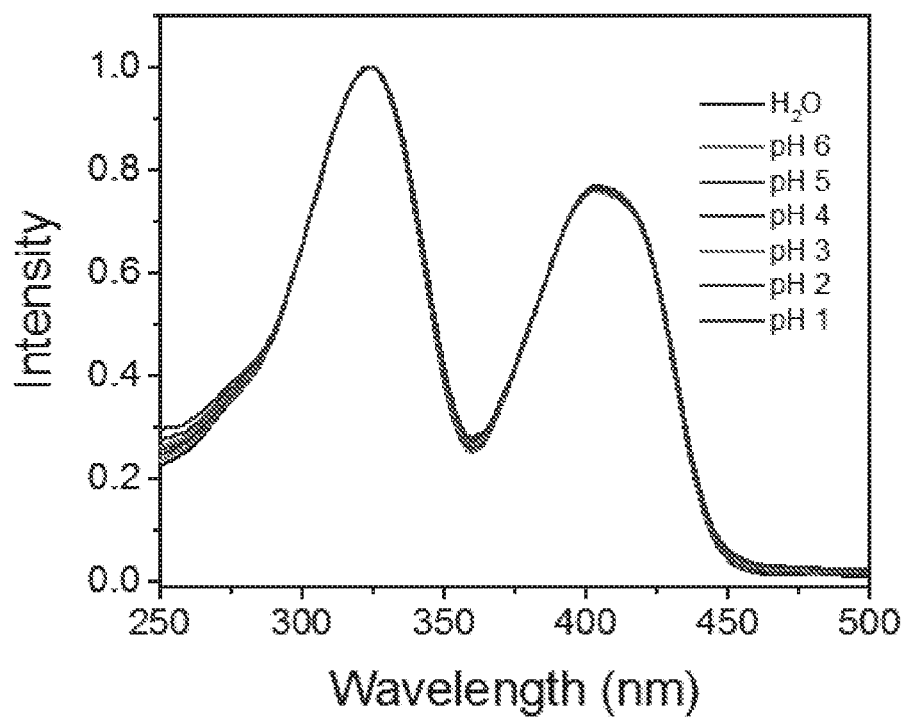
FIG. 2F-2G. Normalized UV/Vis (FIG. 2F) and fluorescence spectra (FIG. 2G) of 6·4Cl at different pH.
Figure 2G:
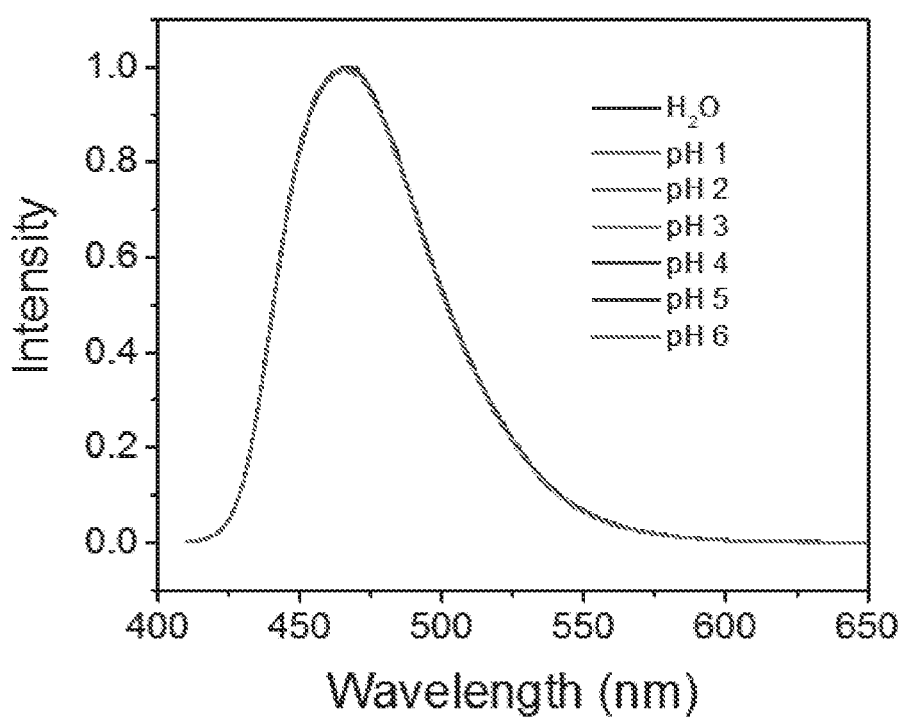

In order to investigate the excited-state properties of $6^{4+}$, especially in relation to its fluorescence quantum yield of unity, we applied femtosecond and nanosecond transient absorption—fsTA and nsTA, respectively—to 6·4Cl (FIG. 2X-2Y) as the target compound and 4·2Cl (FIG. 2X-2y) as the reference. Upon photoexcitation at 414 nm, 4·2Cl shows two positive features at ca. 500 and above 800 nm, which can be assigned to the excited-state absorption (ESA) of the reference compound. Meanwhile, two negative bands centered on 390 and 445 nm can be ascribed to ground-state bleaching and stimulated emission, respectively. Global analysis reveals that the nascent singlet excited state undergoes two sequential structural relaxations with timescales of 0.95 and 134 ps, before decaying back to $S_0$. The singlet lifetime is estimated to be 2.14 ns, a value which is consistent with the nsTA (2.1 ns) and time-resolved fluorescence results (2.04 ns). In the case of the target compound 6·4Cl, very similar photo-induced dynamics can be observed (FIG. 2B). The transient features in 6·4Cl strongly resemble those in 4·2Cl, with close structural relaxation timescales (1.18 and 211 ps), as well as a singlet lifetime (2.45 ns), all of which agree well with the nsTA (2.5 ns) and the time-resolved fluorescence (2.15 ns) measurements. The similarities in spectrometric behavior between $6^{4+}$ and $4^{2+}$ indicate unambiguously that no electron transfer occurs within 6·4Cl when excited at 414 nm. Since there are no additional non-emissive relaxation pathways evident for $6^{4+}$, it makes sense that the fluorescence quantum yield of $6^{4+}$ in H$_2$O is unity, a value which is slightly higher (FIG. 2D-2E) than that ($\Phi_F$=0.95) of $4^{2+}$. The observed increase in fluorescence efficiency in $6^{4+}$, relative to that in $4^{2+}$, can also be attributed to the additional rigidity imposed by the cyclophane structure which reduces certain vibrational degrees of freedom responsible for the radiationless internal conversion process.

TABLE 1

Summary of time-resolved fluorescence (TRF), femtosecond transient absorption (fsTA), and nanosecond transient absorption (nsTA) spectroscopies

|  | $6^{4+}$ | $4^{2+}$ |
|---|---|---|
| TRF (ns) | 2.15 | 2.04 |
| fsTA-$\tau_1$ (ps) | 1.18 | 0.95 |
| fsTA-$\tau_2$ (ps) | 211 | 134 |
| fsTA-$\tau_3$ (ns) | 2.45 | 2.14 |
| nsTA (ns) | 2.5 | 2.1 |

For a better understanding of the electronic and fluorescence properties of $6^{4+}$, DFT and TDDFT calculations were carried out at the cam-B3LYP/6-31G** level of theory. The lowest absorption band in $6^{4+}$ is predicted to be the HOMO-LUMO transition, and the electron in both the HOMO and LUMO of $6^{4+}$ is located (FIG. 2H-2K) only in the TzBIPY$^{2+}$ component. This observation supports the transient absorption interpretation, i.e. no charge transfer happens from the p-Xy components to the TzBIPY$^{2+}$ or the ExBIPY$^{2+}$ when $6^{4+}$ is excited at the lowest absorption band.

TABLE 2

Singlet Transitions and Corresponding Energy Gaps as Well as Oscillator Strengths Obtained by TDDFT Calculations

| Excitation | $E_{calc}$ (eV) | f |
|---|---|---|
| $S_1$ HOMO→LUMO (92%) | 3.50 | 1.096 |
| $S_2$ HOMO-1→LUMO + 1 (52%) | 4.30 | 0.954 |

Figure 2L:
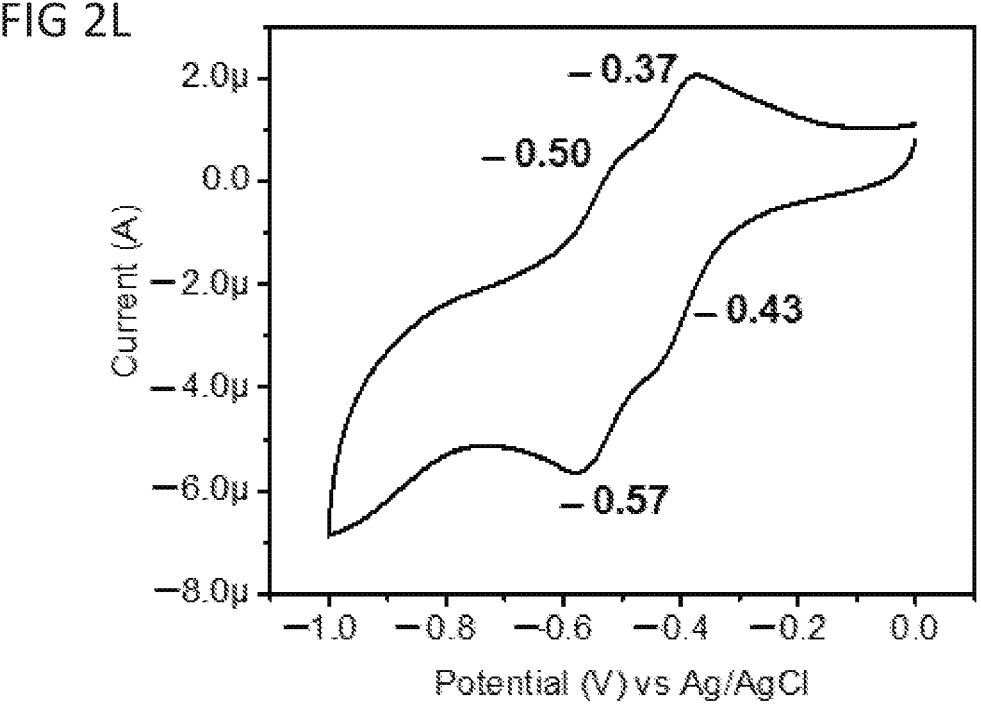
FIG. 2L-2M.
Figure 2M:
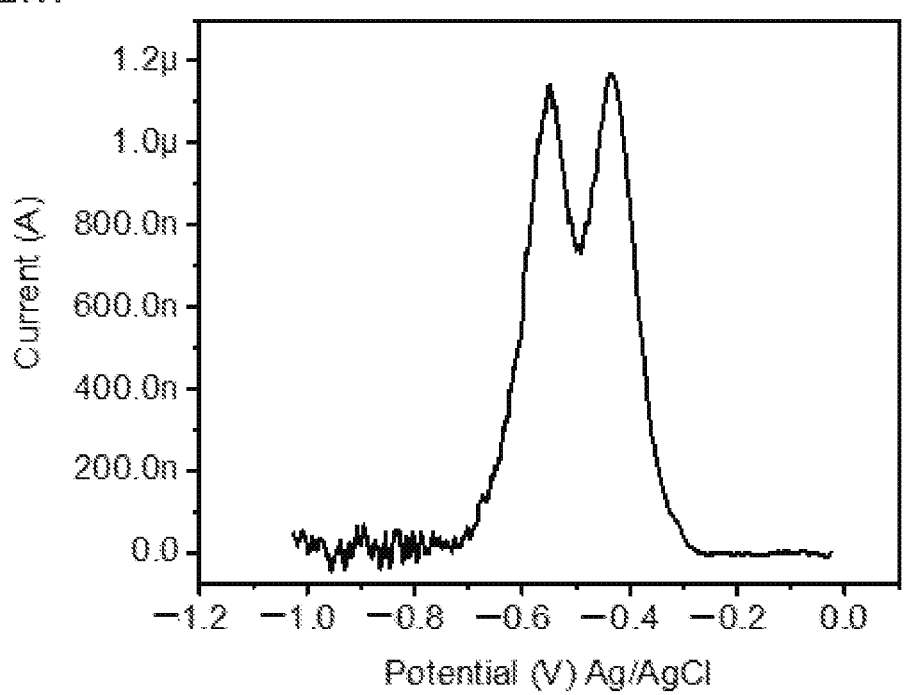
Figure 2N:
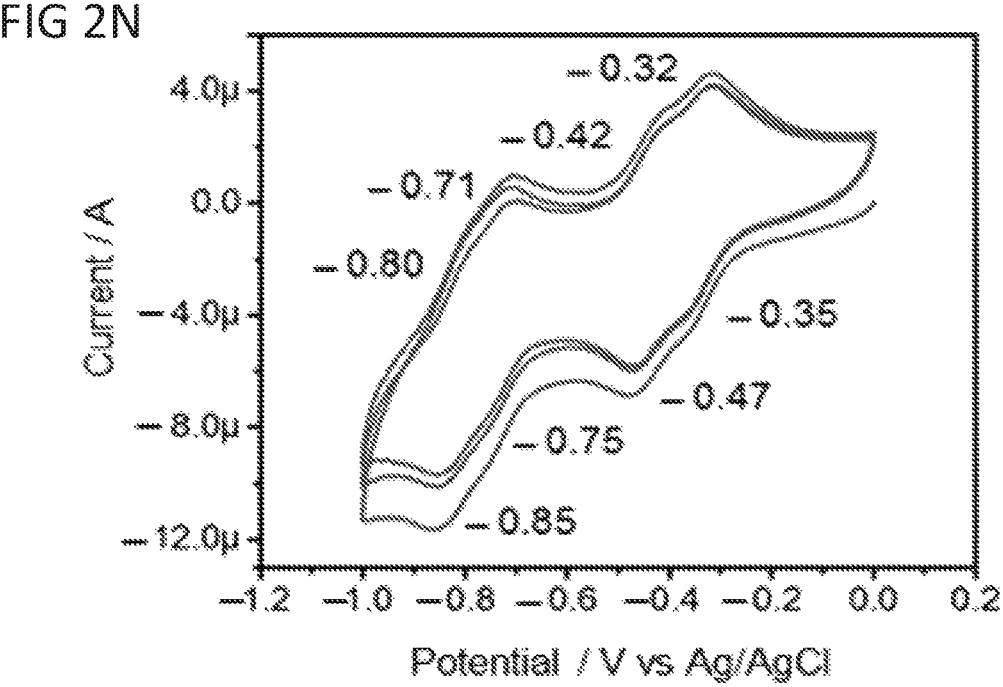
FIG. 2N-2O.
Figure 2O:
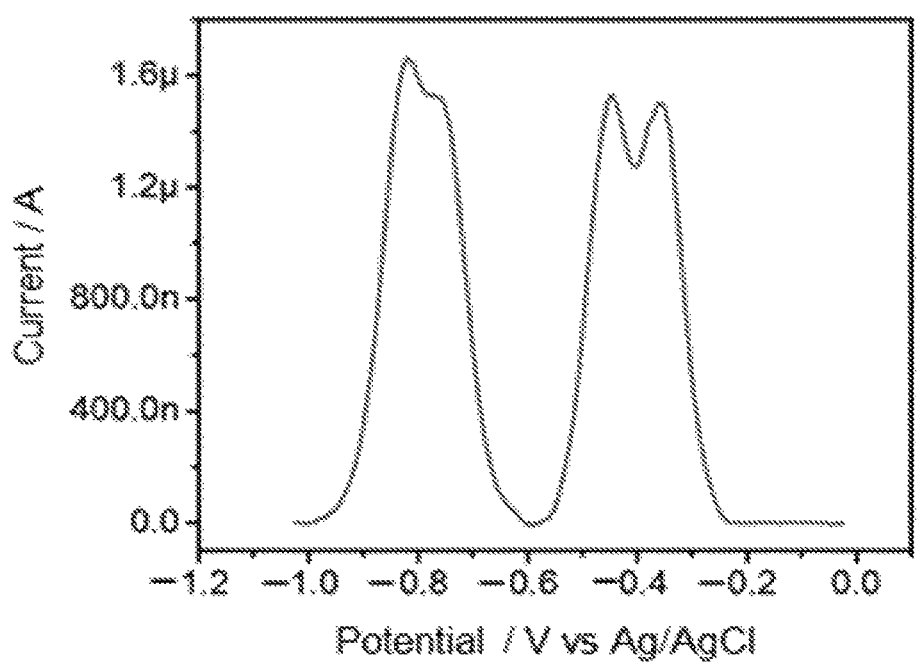

Analysis (FIG. 2C) of the cyclic voltammogram (CV) of hybrid 6·4PF$_6$, reference 4·2PF$_6$ and their comparison with those of the predecessors ExBox·4PF$_6$ and 2·2PF$_6$ provides useful insight into the electrochemical behavior of the hybrid cyclophane which is comprised of two different redox-active units. The CV of 4·2PF$_6$ consists of two reversible two-electron redox couples at −0.43 and −0.57 V, where the potentials of the two cathodic peaks are separated by 140 mV, suggesting that the thiazolo[5,4-d]thiazole unit provides a good electronic communication between the two pyridinium rings (FIG. 2L-2M). On the contrary, the CV of 2·2PF$_6$ consists essentially of one broad redox couple where the two one-electron reduction waves overlap completely at −0.82 V, an observation which indicates that the two bipyridinium redox centers are not communicating and behave quite independently of one another.[23] The hybrid ExTzBox·4PF$_6$, however, consists of four well-separated reversible one-electron redox couples at −0.35, −0.47, −0.75 and −0.85 V, originating from the TzBIPY$^{2+}$ and ExBIPY$^{2+}$ units. The peaks at −0.35 and −0.47 V can be assigned to two one-electron reductions of the TzBIPY$^{2+}$ unit while the peaks at −0.75 and −0.85 V can be assigned to two one-electron reductions of the ExBIPY$^{2+}$ unit. The separation between cathodic and anodic peaks reveals that heterogeneous electron transfer is fast on the timescale of the experiment employing a scan rate of 100 mVs$^{-1}$. This observation reflects the level of electronic communication among the redox centers of TzBIPY$^{2+}$ and ExBIPY$^{2+}$, as well as in between the pyridinium units present within TzBIPY$^{2+}$ and ExBIPY$^2$. This cycle can be repeated multiple times, a situation which suggests (FIG. 2N-2Q) that 6·4PF$_6$ is electrochemically stable. The formation of the first two redox species namely, 6$^{\cdot(3+)}$ and 6$^{2+}$ centered primarily on the Tz ring of the TzBIPY$^{2+}$ unit, whereas the third and fourth one-electron reductions occur on the ExBIPY$^{2+}$ unit, leading to the formation of 6$^{(3\cdot)+}$ and the fully reduced species, is shifted to lower potentials and is therefore more difficult to reduce. The redox potentials determined from CV match (FIG. 2N-2Q) those measured from differential pulse voltammetry (DPV).

Figure 3A:
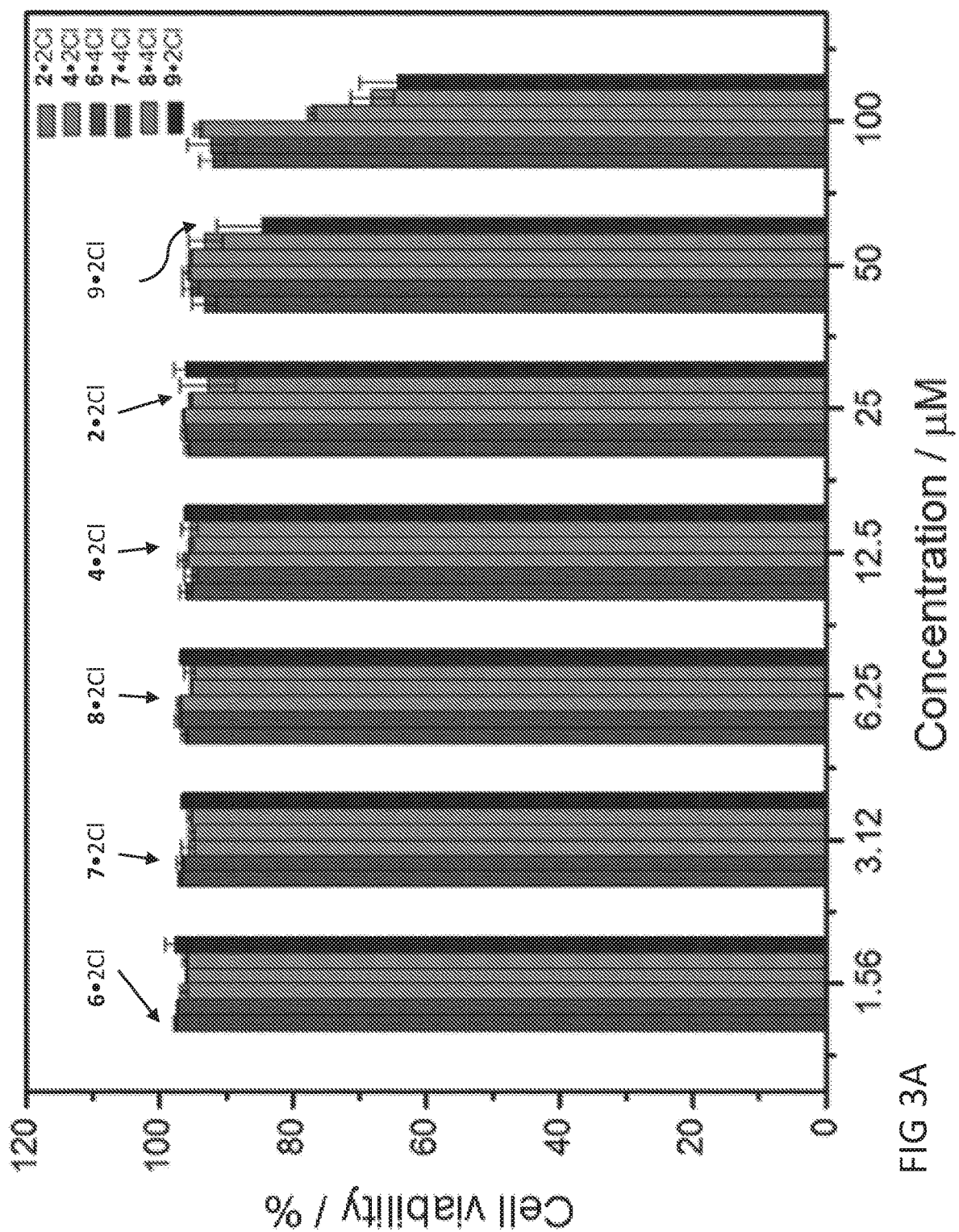
FIG. 3A. Toxicity profiles of rigid cyclophanes 6, 7, 8 and acyclic reference compounds 4, 2 and 9. Effect of different concentrations of all the compounds on RAW 264.7 cells viability after 24 h incubation. The cell viability was assessed by MTT assay. The values presented are the mean±SD (n=3).
Figure 3B:
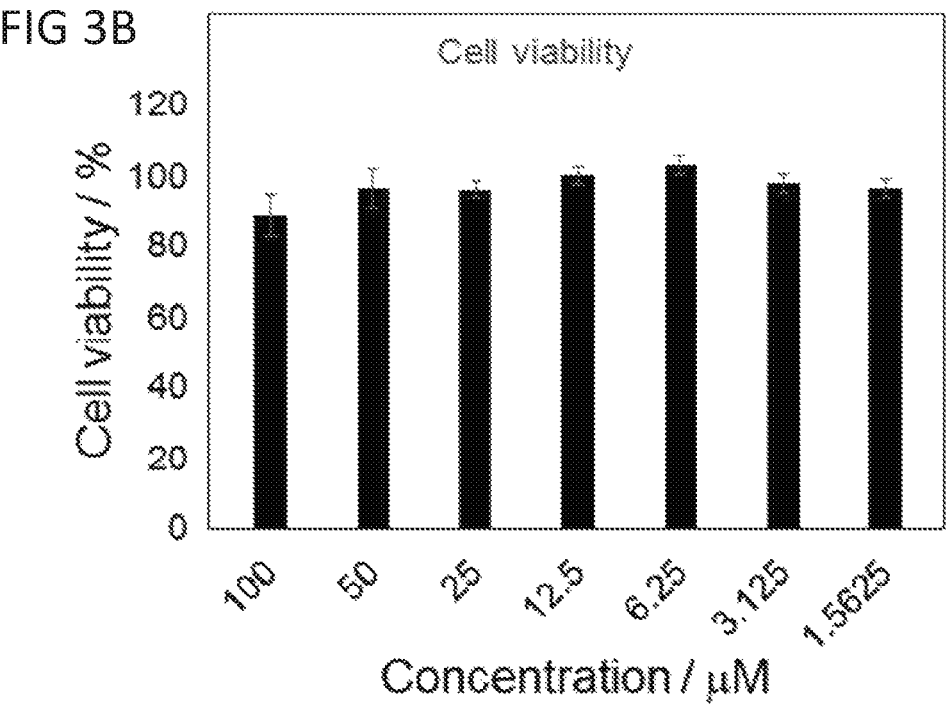
FIG. 3B-3C.
Figure 3C:
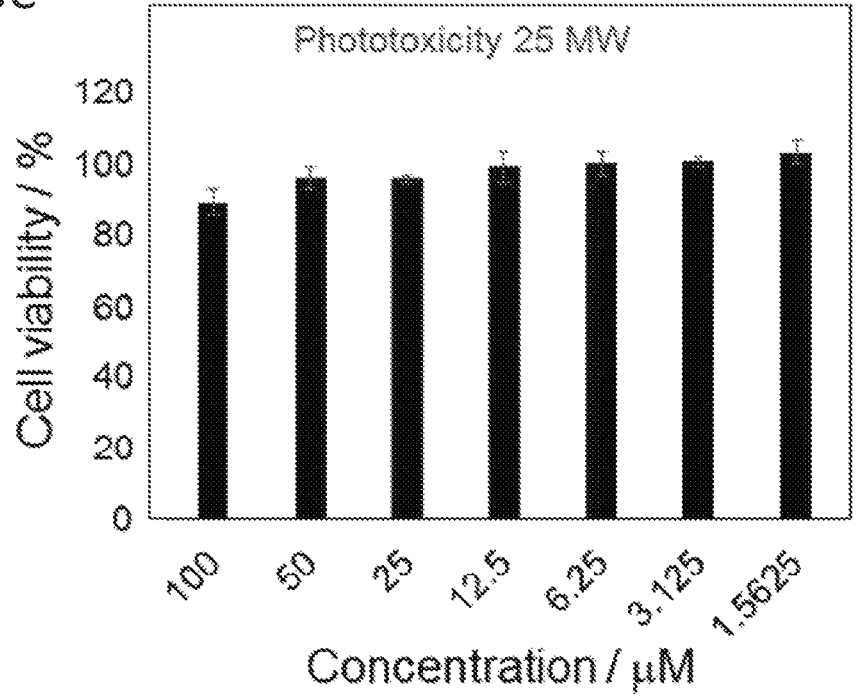
Figure 4Q:
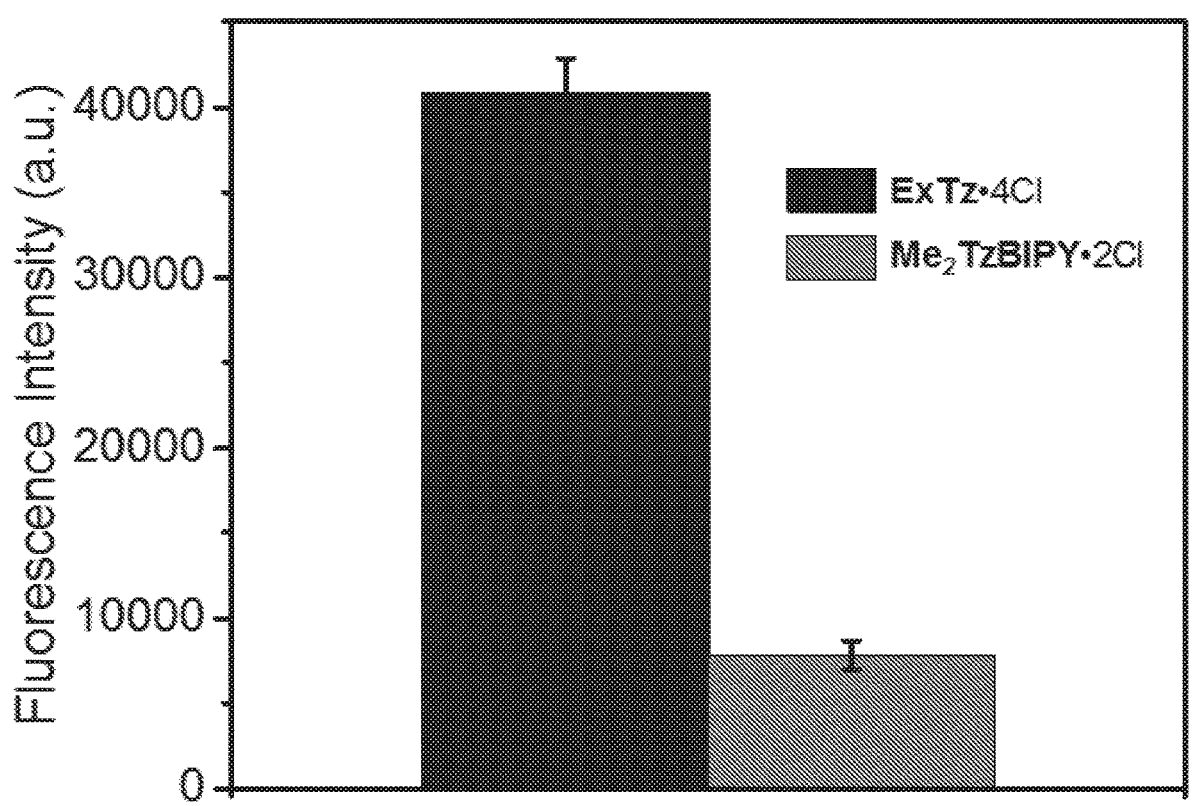
FIG. 4Q. Comparative fluorescence intensity of 6·4Cl and reference 4·2Cl inside live cells.

The bright and highly fluorescent nature of 6$^{4+}$ with a quantum yield reaching unity could potentially make it a good candidate for live-cell imaging. It has to be non-cytotoxic, however, to cells or, in other words, cells should be viable in the presence of 6$^{4+}$ and behave normally. Polycyclic aromatic compounds are known[33] to intercalate into the DNA and small molecules tend to bind double-stranded DNA by virtue of different means including electrostatic attractions, and intercalation between base pairs. Theses interactions hinder the function of various enzymes and thereby induce toxicity to the living cells. We anticipated that, in comparison to the small cationic reference molecules, the rigid box-like structure of 6$^{4+}$, is less likely to intercalate into the DNA and may therefore possess less toxicity. We decided to investigate the in vitro toxicity of 6·4Cl using an MTT (3-(4,5-dimethylthiazol-2-yl)-2,5-diphenyltetrazolium bromide) assay. After a 24 h incubation of RAW 264.7 cells with different concentrations of 6.4Cl and the references 4·2Cl and 2·2Cl, the MTT assays were performed. The experimental results suggest that 6·4Cl is less cytotoxic when compared with 4·2Cl and 2·2Cl. At a 100 μM loading concentration with 6·4Cl, the cell viability is ~93% (FIG. 3A), whereas, for the references 4·2Cl and 2·2Cl, the viabilities were reduced to ~75% and 68%, presumably because the box-like rigid structure prevents 6$^{4+}$ from intercalating into the DNA unlike the reference compounds. We observed a similar trend for other rigid cyclophanes BlueBox and ExBox as well (FIG. 3B-3C). For example, at 100 μM loading concentration of BlueBox, the viability of the RAW 264.7 cells is over 96%, however in the case of the reference dimethyl viologen, popularly known as paraquat, only ~63% of cells remain viable, an observation which matches with paraquat toxicity reported elsewhere in literature.[34] The cell viability of 6·4Cl obtained from MTT assay was further confirmed by a fluorescence-based Calcein AM cell viability assay (FIG. 3B), as the presence of chromophores may influence MTT assay results. Furthermore, no phototoxicity of 6·4Cl was observed when RAW 264.7 cells were incubated with different concentrations of 6·4Cl and irradiated with light (410 nm, 25 mW) for 15 min (FIG. 3C). It is indeed an important observation for understanding the cytotoxicity of this important class of cyclophanes and exploring their biological applications.

Based on the MTT results, a 20-50 μM concentration range of 6·4Cl was used for all the imaging experiments. In order to understand the ability of 6$^{4+}$ to be internalized by cells, RAW 264.7 cells were incubated with 6·4Cl (20 μM in PBS solution) for 4 h, followed by imaging with a confocal microscope. The acquired images showed brilliant blue emission in the cytoplasm of the cells, without altering their morphologies. For a better understanding of the internalization, 6·4Cl was incubated with the cells in presence of a nuclei stain, SYTO nuclei. The blue fluorescence signal was localized predominantly in punctae at the perinuclear region of the cells (FIG. 4A-4D), whereas red fluorescence was observed from the nuclei. Incubation of a concentrated solution (50 μM) of 6·4Cl with the cells also showed bright blue fluorescence, an observation which demonstrates that different concentrations of 6·4Cl could be used (FIG. 4I-4L) for cell imaging. This successful membrane penetration could be attributed to the tetracationic nature of the 6$^{4+}$.

In order to gain further evidence of cellular localization in detail, 6·4Cl was incubated with cells in the presence of a lysosomal marker, Lyso Tracker green. Confocal microscopy images showed (FIG. 4E-4H) significant co-compartmentalization of the green (Lyso Tracker green) and blue (6·4Cl) channel emission coming from the lysosomes. A zoomed-in section (FIG. 4H) shows the presence of 6$^{4+}$ in the lysosome, alongside Lyso Tracker green. In the control experiment, only a little fluorescence (FIG. 4M-4P) was detected with the reference compound 4·2Cl upon cell incubation. In fact, the fluorescence inside the cells of the reference 4·2Cl was quenched within 3 s of laser irradiation and lost its imaging capability. This observation implies the importance of box-like rigid structures in preventing photobleaching under live-cell imaging conditions.

We have demonstrated a facile synthesis and complete characterization of a rationally designed hybrid cyclophane, 6$^{4+}$, in a template free manner. The 6·4Cl is highly water-soluble and possesses bright blue fluorescence with a quantum yield of unity when excited at the lowest absorption band, an observation which can be ascribed to no electron transfer from the p-Xy components to the TzBIPY$^{2+}$ or the ExBIPY$^{2+}$ unit, as revealed by time-resolved spectroscopic measurements. The 6·4Cl is extremely photostable in H$_2$O, endures strong acidic conditions, and operates in a broad pH range without any change of its fluorescence characteristics. MTT assay shows a greater than 90% cell viability after 24 h incubation with 6·4Cl at a loading concentration as high as 100 μM. Taken all together, the potentials of the rigid cyclophane 6$^{4+}$ for live-cell imaging could be easily understood. Confocal microscopy images reveal that 6$^{4+}$ is efficiently taken up by the RAW 264.7 cells into their lysosomal compartments and exhibits bright blue fluorescence without any hint of photobleaching. Furthermore, the fluorescence of 6$^{4+}$ is six times brighter inside the cells than that of the reference 4$^{2+}$ whose fluorescence is completely quenched within 3 s under imaging conditions. Our findings may assist the understanding of the fundamental principles for designing this new class of imaging probes by recognizing the underlying competitive photophysical processes in the context of hybrid and rigid molecular geometries. Here, we note that 6·4Cl is first of its kind to be utilized for live cell imaging and has good potential in the field of imaging. Several challenges, however, must still be addressed, such as improving the absorbance window for better penetration, and active targeting, which is necessary for in-depth in vivo imaging. We believe that the proper choice of building units and fine-tuning of the fluorophore structure within the cyclophane structures may address these challenges. In a broader perspective, the in vitro cell studies strongly support the importance of using box-like rigid cyclophanes for live-cell imaging and could well be the stepping stone for developing a new class of imaging probes for multiple modalities in addition to fluorescence imaging. It is also worth mentioning that the cavity of 6$^{4+}$ may be utilized to incorporate different guest molecules, with various imaging modalities such as photoacoustic, ultrasound, PET or MRI, leading to the development of supramolecular multimodal-imaging platforms. Guest molecules having therapeutic properties could also be incorporated inside the cyclophane cavity, which holds promise for the development of supramolecular theranostic agents.

Definitions

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of a cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)N\ R^2\ R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus>10% of the particular term.

As used herein, the tens "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Materials/General Methods/Instrumentation

All chemicals and reagents were purchased from commercial suppliers (Aldrich or Fisher) and used without further purification. 4,4'-(1,4-Phenylene)bispyridine (ExBIPY), bisbromomethyl(bis-p-benzyl-4,4'-(1,4-phenylene)bispyridine)bis(hexafluorophosphate) (DB·2PF$_6$), 2,5-di(pyridin-4-yl)thiazolo[5,4-d]thiazole (TzBIPY) were prepared according to previous literature procedures[1,2] with slight modifications. The synthesis of the hybrid cyclophane ExTz·4PF$_6$ (6·4PF$_6$), the counterion exchanged product ExTz·4Cl (6·4Cl), the reference Me$_2$TzBIPY·2PF$_6$ (4·2PF$_6$) and the counterion exchanged product Me$_2$TzBIPY·2Cl (4·2Cl) are described in the Section B on synthetic protocols. Thin layer chromatography (TLC) was performed on silica gel 60 F254 (E. Merck). Column chromatography was carried out on silica gel 60F (Merck 9385, 0.040-0.063 mm). High-resolution mass spectra were measured on an Agilent 6210 Time of Flight (TOF) LC-MS, using an ESI source, coupled with Agilent 1100 HPLC stack, using direct infusion (0.6 mL/min). Nuclear magnetic resonance (NMR) spectra were recorded on a Bruker Avance 600 and Varian P-Inova 500 spectrometers, with working frequencies of 500 and 600 MHz, respectively. Chemical shifts were reported in ppm relative to the signals corresponding to the residual nondeuterated solvents (CD$_3$CN: δ 1.94 ppm).

UV/Vis Absorption spectra were recorded using a UV-3600 Shimadzu spectrophotometer. Steady-state emission spectra were acquired using HORIBA Nanolog spectrofluorimeter equipped with an integrating sphere for absolute photoluminescence quantum yield determination and time-correlated single-photon counting (TCSPC) module for emission decays of 4·2Cl in H$_2$O. The time-resolved fluorescence (TRF) measurement of 6·4Cl in H$_2$O was carried out with a streak camera system (Hamamatsu C4334 Streakscope).

The setup for transient absorption measurements has been described elsewhere.[3] Photoexcitation pulses (414 nm) were obtained through a BBO crystal doubling the fundamental beam for the measurements. The pulse power for photoexcitation was attenuated to ~1 pJ/pulse, using neutral density filters. The pump polarization was randomized employing a commercial depolarizer (DPU-25-A, Thorlabs, Inc.) to eliminate any orientational dynamics contributions from the experiment. All the spectra were collected on a commercial spectrometer (Ultrafast Systems, LLC Helios and EOS spectrometers, for fsTA and nsTA, respectively). All samples were stirred to avoid localized heating or degradation effects. The optical density was maintained around 0.5 for all samples.

Cyclic Voltammetry (CV) experiments were carried out at room temperature in Ar-purged solutions of dry MeCN with a Gamry Multipurpose instrument (Reference 600) interfaced to a PC. All CV experiments were performed using a glassy carbon working electrode (0.071 cm$^2$). The electrode surface was polished routinely with 0.05 μm alumina-water slurry on a felt surface immediately before use. Platinum wire (Pt) and Ag/AgCl electrode were used as counter electrode and reference electrode respectively. The concentration of the sample and supporting electrolyte, tetrabutylammonium hexafluorophosphate (TBAPF$_6$), were 1.0 mM and 0.1 M, respectively. The CV cell was dried in an oven immediately before use, and Ar was continually flushed through the cell as it was cooled down to room temperature to avoid condensation of H$_2$O.

All DFT and TDDFT calculations were performed at the cam-B3LYP/6-31G** level with the Q-Chem 4.3 package.[4] Geometry optimizations were performed without symmetry constraints. The molecular orbitals were generated with IQmol and displayed in FIG. 2H-2K along with the molecular orbitals.

Synthetic Protocols 1) 2,5-Di(pyridin-4-yl)thiazolo[5,4-d]thiazole (3)

SCHEME 2. Synthesis of 2,5-di(pyridin-4-yl)thiazolo[5,4-d]thiazole-TzBIPY (3).

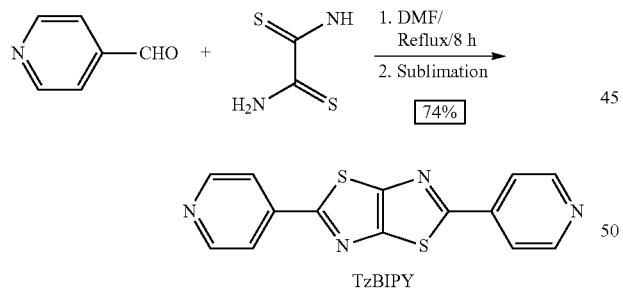

The synthetic protocol was adopted according to the literature procedure[2], except that a slightly modified method was used as follows. A solution of dithiooxamide (200 mg, 1.6 mmol) and 4-pyridinecarboxaldehyde (0.40 mL, 4.4 mmol) in anhydrous dry DMF (10 mL) was heated under reflux for 4 h at 150° C. Upon cooling, the product was precipitated out from the resulting solution. Filtration and washing with H$_2$O afforded TzBIPY as yellow solid in 74% yield. $^1$H NMR (500 MHz, CDCl$_3$, 25° C.) δ=8.77 (d, J=5.0 Hz, 2H), 7.86 (d, J=6.0 Hz, 4H). $^{13}$C NMR (125 MHz, CDCl$_3$, 25° C.) δ=167.5, 152.3, 151.0, 140.4, 120.1.

2) 4,4'-(Thiazolo[5,4-d]thiazole-2,5-diyl)bis(1-methylpyridinium) (4)

SCHEME 3. Synthesis of 4·2PF$_6$.

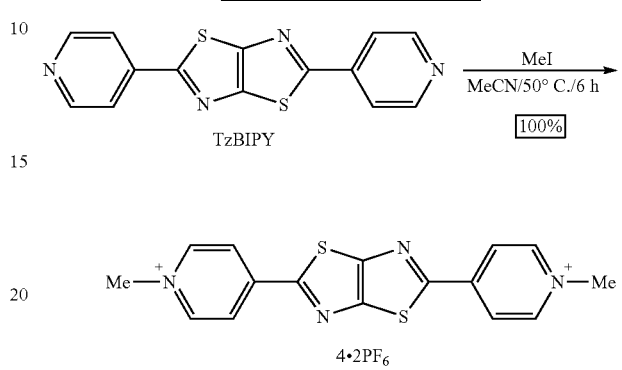

An MeCN (5 mL) solution of TzBIPY (50 mg, 0.17 mmol) was introduced into a round bottomed flask and excess of MeI was added to the flask and was stirred at 50° C. for 6 h. Then reaction mixture was cooled down to room temperature, the precipitate was filtered and the unreacted MeI was removed with multiple hexane washes to obtain the pure 4-2I in 100% yield. Finally, 4·2I was dissolved in H$_2$O and 4·2PF$_6$ was reprecipitated by adding solid NH$_4$PF$_6$ salt, and collected by filtration. $^1$H NMR (500 MHz, CD$_3$CN, 25° C.) δ=8.80 (d, J=6.5 Hz, 2H), 8.58 (d, J=6.0 Hz, 4H), 4.38 (s, 6H). Water soluble 4-2Cl was synthesized following a similar couterion exchange procedure. 4·2PF$_6$ was dissolved in MeCN and 4·2Cl was reprecipitated by adding solid tetrabutylammonium chloride salt, and collected by filtration.

3) Bisbromomethyl(bis-p-benzyl-4,4'-(1,4-phenylene)bispyridine)bis(hexafluorophosphate) =DB·2PF$_6$ (5)

SCHEME 4. Synthesis of DB·2PF$_6$ (5·2PF$_6$)

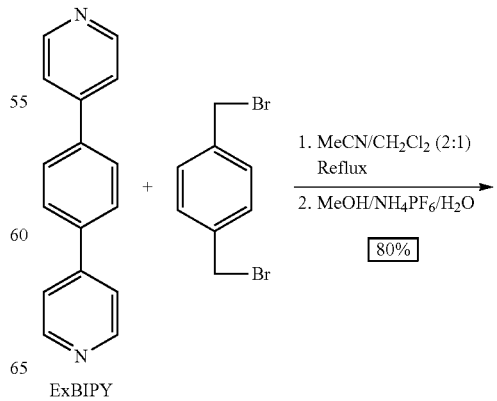

-continued

4 ExTz·4PF$_6$ or ExTzBox (6)

Scheme 5. Synthesis of 6·4PF$_6$.

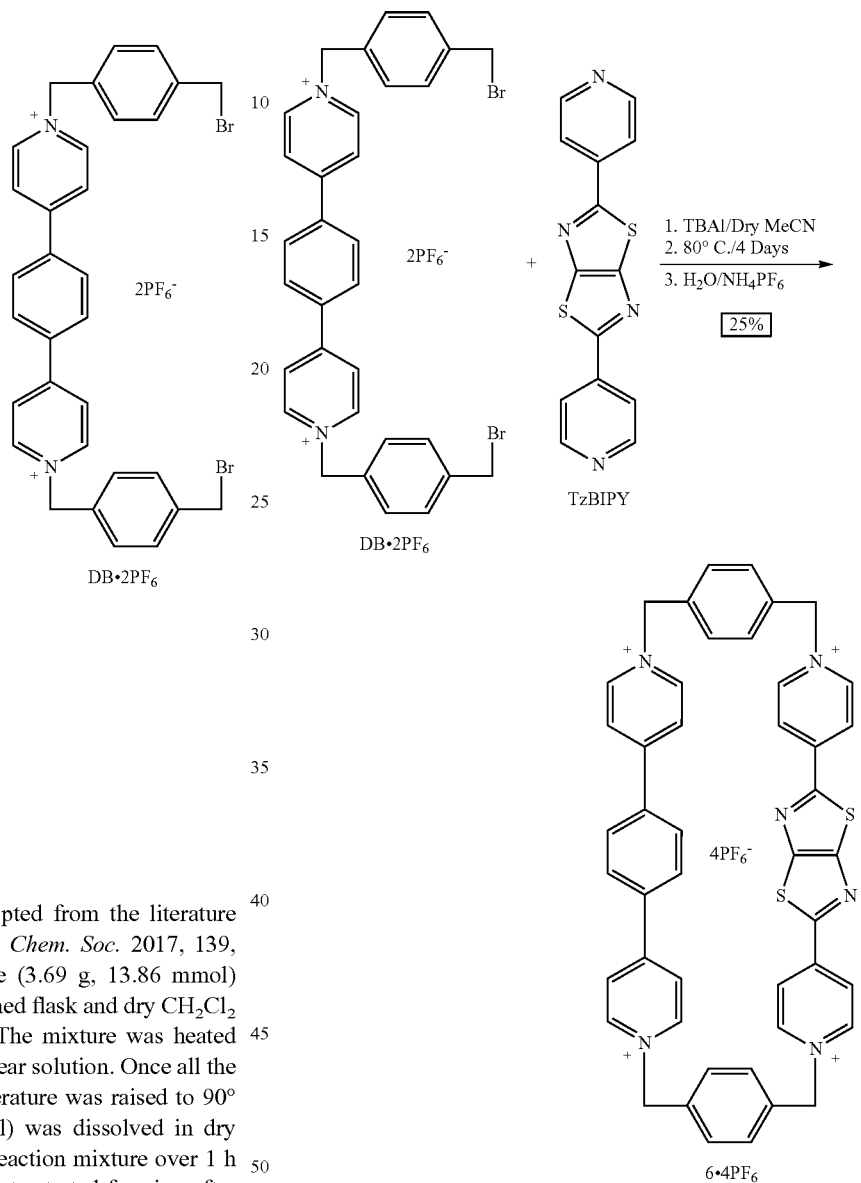

The synthetic protocol was adopted from the literature procedure.[Gong, X. et al., *J. Am. Chem. Soc.* 2017, 139, 4107-4116] α,α-Dibromo-p-xylene (3.69 g, 13.86 mmol) was introduced into a round-bottomed flask and dry CH$_2$Cl$_2$ (30 mL) was added to the flask. The mixture was heated under reflux at 50° C. to obtain a clear solution. Once all the chemicals had dissolved the temperature was raised to 90° C. ExBIPY[1] (322 mg, 1.38 mmol) was dissolved in dry MeCN (60 mL) and added to the reaction mixture over 1 h (4-5 portions). The yellow precipitate started forming after 30 min. The reaction mixture was stirred for 2 days at 90° C. Then it was brought to the room temperature and the yellow precipitate was filtered off and washed with CH$_2$Cl$_2$ to remove the unreacted starting materials. Finally, the solid was dissolved in H$_2$O and excess of NH$_4$PF$_6$ was added to precipitate the crude product. Excess of NH$_4$PF$_6$ was washed several times with H$_2$O to obtain the pure whitish yellow product in 80% yield. $^1$H NMR (500 MHz, CD$_3$CN, 25° C.): δ=8.80 (AA' of AA'XX', J=7 Hz, 4H), 8.33 (XX' of AA'XX', J=6.5 Hz, 4H), 8.12 (s, 4H), 7.55 (AA' of AA'BB', J=8 Hz, 4H), 7.47 (BB' of AA'BB', J=8.5 Hz, 4H), 5.73 (s, 4H), 4.61 (s, 4H). $^{13}$C NMR (125 MHz, CD$_3$CN, 25° C.): δ=155.0, 144.3, 139.9, 136.7, 132.9, 129.8, 129.1, 129.1, 125.6, 63.1, 32.3.

DB·2PF$_6$ (0.194 g, mmol), TzBIPY (59 mg, mmol) and TBAI (0.016 g, mmol) were introduced into round-bottomed flask and dry MeCN (180 mL) was added to the flask. The mixture was stirred at 80° C. for 4 days. The reaction mixture was brought to room temperature and excess of NH$_4$Cl was added to precipitate a yellow solid. The precipitate was filtered off and washed with Me$_2$CO and CH$_2$Cl$_2$ to remove tetrabutylammonium salt. The solid was dried and then dissolved in H$_2$O, and reprecipitated as PF$_6^-$ salt by adding solid NH$_4$PF$_6$ (~5% (w/v)). The excess of NH$_4$PF$_6$ was removed by multiple washes with H$_2$O. Finally, pure ExTz·4PF$_6$ was obtained after running a reverse-phase chromatography column using H$_2$O/MeCN (9:1 v/v) in 25% yield as a yellow solid. ExTz·4Cl was precipitated by dissolution of ExTz·4PF$_6$ in MeCN, followed by counterion exchange by tetrabutylammonium chloride treatment. $^1$H NMR (500 MHz, CD$_3$CN, 25° C.) δ=8.92 (d, 6.5 Hz, 4H), 8.78 (d, 6.5 Hz, 4H), 8.41 (d, 6.5 Hz, 4H), 8.19 (d, 6.5 Hz, 4H), 7.94 (d, 4H), 7.66 (dd, 4 Hz, 8H), 5.76 (s, 4H), 5.70 (s, 4H). $^{13}$C NMR (125 MHz, CDCl$_3$, 25° C.) δ=165.4, 156.8, 155.1, 148.0, 145.6, 144.9, 137.0, 136.8, 136.4, 131.0, 130.5, 129.7, 126.2, 125.5, 65.0, 64.4. HRMS-ESI (m/z) for ExTz·4PF$_6$: Calcd for C$_{46}$H$_{36}$F$_{24}$N$_6$P$_4$S$_2$: m/z=513.0863 [M–2PF$_6$]$^{2+}$; found: 513.0870 [M–2PF$_6$]$^{2+}$, 1171.1368 [M–PF$_6$]$^+$; found 1171.1383 [M–PF$_6$]$^+$.

Crystallographic Characterization a) Method: Single crystals of 6·4PF$_6$ were grown by slow vapor diffusion of $^i$Pr$_2$O into a solution of 6·4PF$_6$ in MeCN over the course of 3 days. A suitable single crystal was selected and mounted in inert oil and transferred to the cold gas stream of a Kappa Apex 2 diffractometer. The crystal was kept at 100 K during data collection. Using Olex2, the structure was solved with the ShelXT structure solution program using Direct Methods and refined with the ShelXL refinement package using Least Squares minimization.

b) Crystal Data: Monoclinic, space group P2$_1$ (no. 4), a=10.8385(14), b=18.879(3), c=13.905(2) Å, V=2843.6(7) Å$^3$, Z=2, T=100 K, μ(MoKα)=0.333 mm$^{-1}$, D$_{calc}$=1.679 g/mm$^3$, 9600 reflections measured (2.93≤2Θ≤50.00), 7923 unique (R$_{int}$=0.0830, R$_{sigma}$=0.0536) which were used in all calculations. The final R$_1$ was 0.0892 (I>2σ(I)) and wR$_2$ was 0.2429 (all data).

c) Refinement Details: The enhanced rigid-bond restraint (RIGU) was applied globally. Several ill-behaved carbon atoms were refined with additional displacement parameter restraints (DELU, SIMU, and ISOR).

Fluorescence Spectroscopy

The kinetic analysis of the time-resolved data (FIG. 2D-2G) is based on a global fit to selected single-wavelength/frequency kinetics. Several kinetic traces at different wavelengths/frequencies were chosen and fitted globally to a kinetic model. The MATLAB program solves the differential equations, then convolutes them with the instrument response function, before employing a least-squares fitting to find the parameters which result in fits to the same functions for all selected wavelengths/frequencies. Once these parameters are established, they are fed directly into the differential equations, which were solved for the populations of the states in model—i.e., A(t), B(t), C(t), and D(t). Finally, the raw data matrix (with all the raw data) is deconvoluted with the populations as functions of time to produce the species-associated spectra. See, TABLE 1.

Cyclic Voltammetry

All cyclic redox-potential curves were measured in dry and degassed MeCN solutions of 6·4PF$_6$ and 4·2PF$_6$ in the presence of 0.1 M tetrabutylammonium hexafluorophosphate using a fixed scan rate of 0.1 Vs$^{-1}$. The CV of 6·4PF$_6$ shows (FIG. 2N-2O) reduction peaks at −0.35, −0.47, −0.75 and −0.85 V. The proposed assignments are illustrated in the chemical formulae below. The peaks at −0.35 and −0.47 V are assigned to two one-electron reduction of the TzBIPY$^{2+}$ unit and the peaks at −0.75 and −0.85 V and are assigned to two one-electron reductions of the ExBIPY$^{2+}$ unit. The 4·2PF$_6$ shows (FIG. 2L-2M) two one-electron reduction peaks at −0.43, −0.57 V respectively.

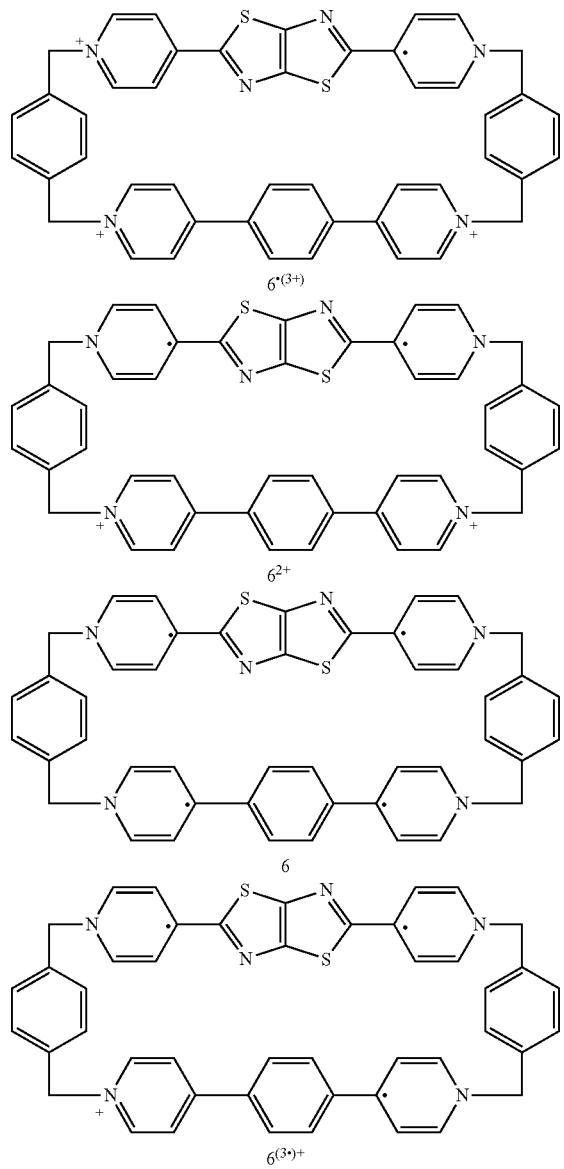

Cell Viability Study

Cell culture: Murine macrophages (RAW 264.7 cells) that were obtained from the American Type Culture Collection (ATCC, Rockville, MD, USA) were utilized for cell culture experiments. These cells were cultured in Dulbecco's Modified Eagle's Medium (DMEM) supplemented with 10% fetal bovine serum (FBS), penicillin (100 IU/mL) and streptomycin (100 μg/mL) at 37° C. in the presence of air (95%) and carbon dioxide (5%).

MTT Assay: RAW 264.7 macrophages (2×10$^5$ cells/mL, 100 μL) were seeded in each well of a 96-well plate. 10 μL of samples in PBS was added to each well to achieve different concentrations (100, 50, 25, 12.5, 6.25, 3.125 and 1.56 μM). After 24 h incubation, each well was added with MTT (5 mg/ml in PBS, 10 μL) and then incubated for 4 h. The media from each well was pipetted out, formazan crystals deposited on the plate were dissolved in 200 μL of dimethyl sulfoxide and the absorbance of each well was measured using a microplate reader at 560 nm.

All the samples were analyzed in quadruplicates. The percentage cell viability was then calculated using the formula: % cell viability=(OD of treated sample/OD of the untreated sample)*100.

Calcein AM Cell viability assay: RAW 264.7 macrophages ($2\times10^5$ cells/mL, 100 μL) were seeded in each well of a Black 96-well plate. Cyclophane $6^{4+}$ in PBS (10 μL) was added to each well to achieve different concentrations (100, 50, 25, 12.5, 6.25, 3.125 and 1.56 μM). After 24 h of incubation, cells were washed twice with PBS, added with Calcein AM (1 μM, 100 μL in PBS) to each well and then incubated for 1 h in the dark. After incubation, fluorescence intensity of each well was measured using a microplate reader at excitation and emission wavelengths of 495 and 515 nm, respectively. The measured fluorescence intensity (FI) is proportional to the number of viable cells.

The percentage cell viability was then calculated using the formula: % cell viability=(FI of treated sample/FI of untreated sample)*100.

Phototoxicity studies: RAW 264.7 macrophages ($2\times10^5$ cells/mL, 100 μL) were seeded in each well of a Black 96-well plate. Cyclophane $6^{4+}$ in PBS (10 μL) was added to each well to achieve different concentrations (100, 50, 25, 12.5, 6.25, 3.125 and 1.56 μM). After 24 h incubation, wells were washed with PBS, added with 100 μL of DMEM and immediately irradiated with visible light using Max-303 Xenon Light Source (410 nm, Asahi Spectra) at a light intensity of 25 MW for 15 min. Following irradiation cells were incubated overnight and viability was measured using Calcein AM as described above.

Live Cell Confocal Microscopy

RAW 264.7 macrophages ($1\times10^5$ cells/mL, 475 μL) were plated in each well of a 4 well p-slide (ibidi cell focus) and cultured overnight. Samples (1 mM in PBS, 25 μL) were added to each well and incubated for 4 h. After incubation, cells were washed with phenol free DMEM and stained with LysoTracker green (lysosome stain) or SYTO nuclei (nuclear stain) at 1:10,000 dilutions. Controls used were cells added with only stains, cells only and cells with materials only. Plated cells were imaged within a humidified chamber using a 100× oil-immersion objective on an SP5 Leica Confocal Microscope using HyD detectors and lasers: 405 nm diode laser for material, 561 nm HeNe laser for Lysotracker green, and 633 nm HeNe laser for SYTO 61.

UV Light Photobleaching

Figure 5A:
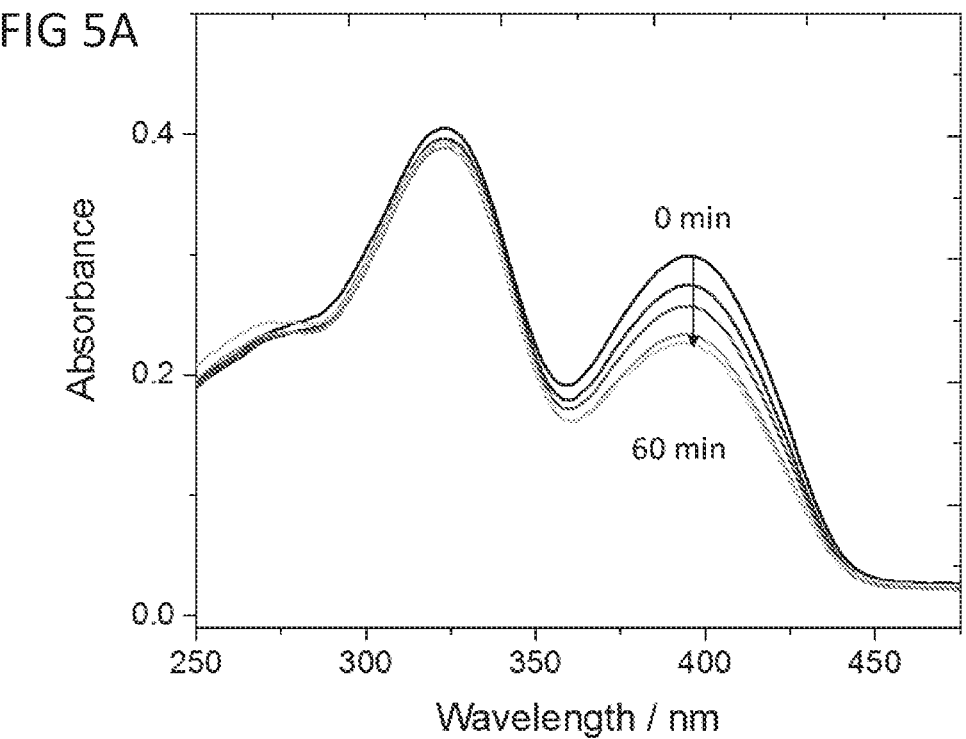
FIG. 5A-5B. Photobleaching studies of 6·4Cl (FIG. 5A) and commercially available hoechst 33258 (FIG. 5B), a nucleic acid staining dye.
Figure 5B:
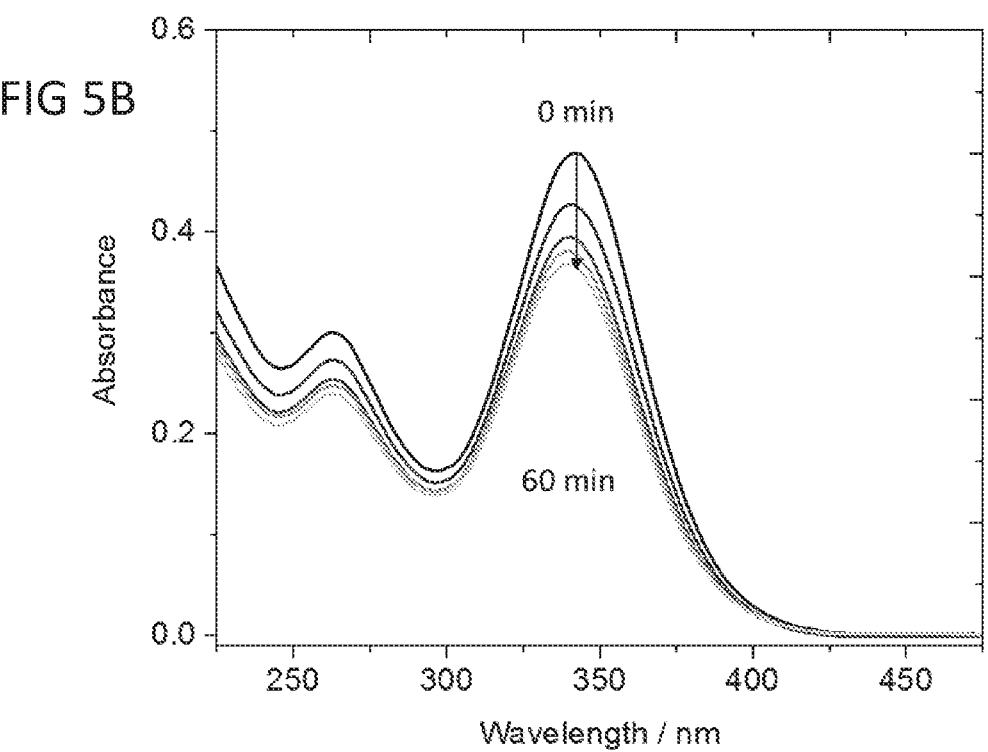
Figure 6A:
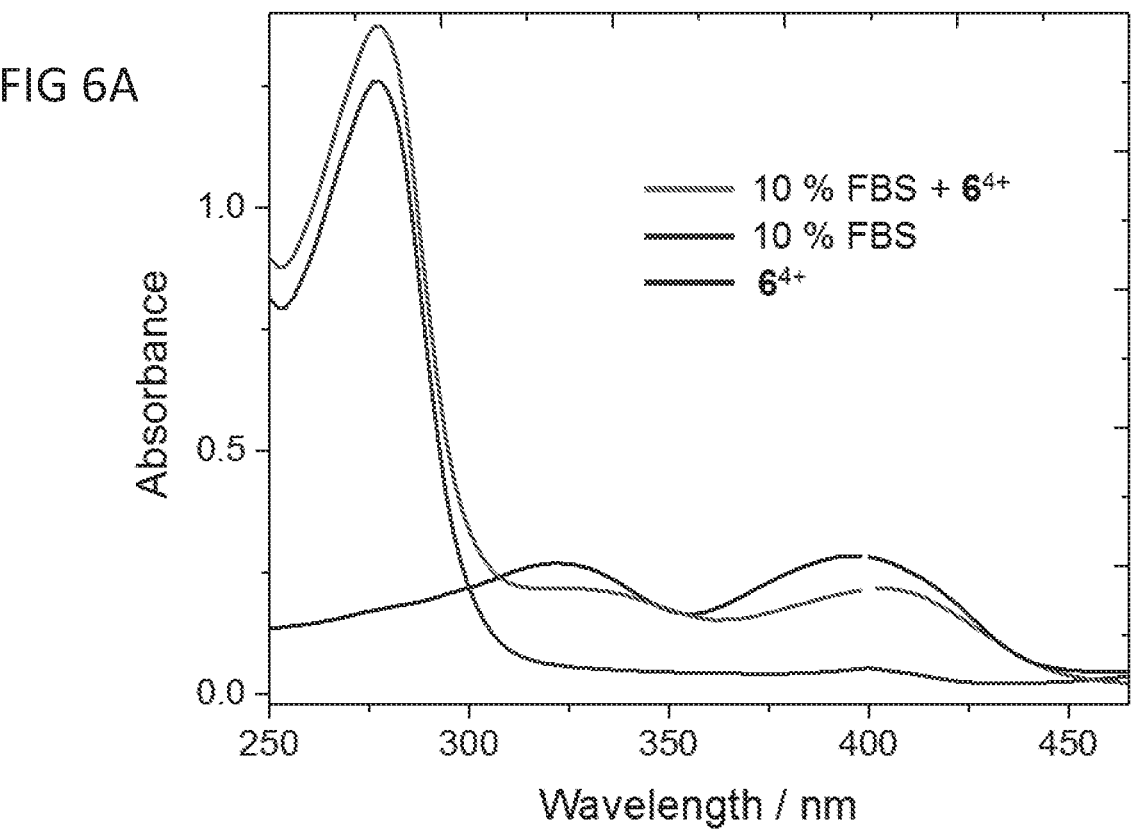
FIG. 6A-6B.
Figure 6B:
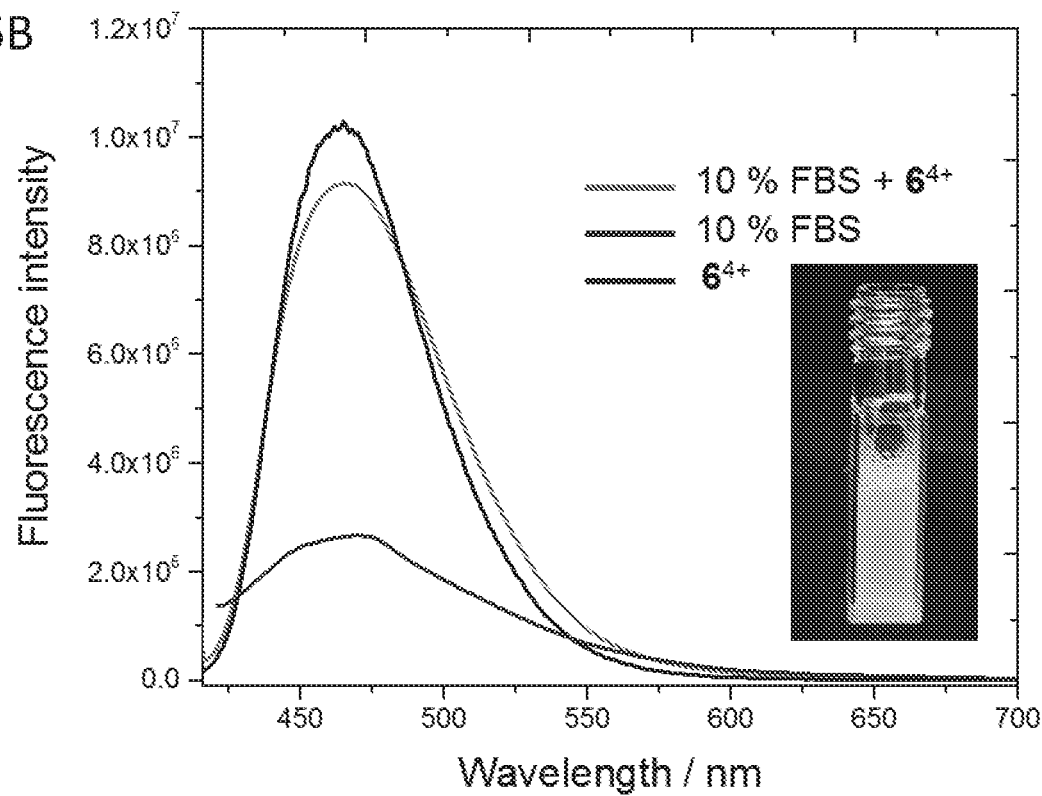

Samples were irradiated with a 18 W LED UV flashlight (395 nm, Hinmay super bright LED). They were immersed in a 23±1° C. water bath during irradiation periods. (FIG. 5A-5B)

We claim:

1. A cyclophane for live-cell imaging, the cyclophane comprising an ordered, cyclic arrangement of a chromophore, a first linker unit, a molecular strut, and a second linker unit,
wherein the chromophore comprises a fluorescent thiazolothiazole unit and the thiazolothiazole unit is:

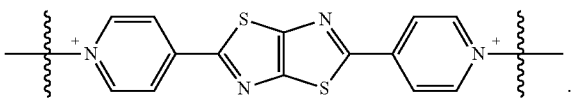

2. The cyclophane of claim 1, wherein
the molecular strut comprises a viologen unit;
the first linker unit and the second linker unit each independently comprise a xylene linker; or any combination thereof the molecular strut comprises a viologen unit and the first linker unit and the second linker unit each independently comprise a xylene linker.

3. The cyclophane of claim 2, wherein the molecular strut comprises the viologen unit and the viologen unit comprises an extended viologen unit.

4. The cyclophane of claim 3, wherein the extended viologen unit comprises

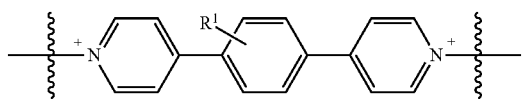

wherein $R^1$ is selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl.

5. The cyclophane of claim 4, wherein $R^1$ is selected from the group consisting of hydrogen, the halogen, amino, a thiophene, and phenyl.

6. The cyclophane of claim 5, wherein the viologen unit comprises

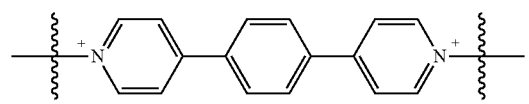

7. The cyclophane of claim 2, wherein the first linker and the second linker each comprise the xylene linker and wherein the first linker and the second linker each comprise

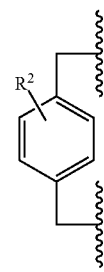

wherein $R^2$ is selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl.

8. The cyclophane of claim 7, wherein $R^2$ is selected from the group consisting of hydrogen, the halogen, amino, a thiophene, and phenyl.

9. The cyclophane of claim 8, wherein the first linker and the second linker each comprise

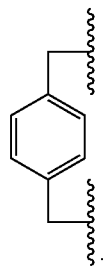

10. The cyclophane of claim 2, wherein the cyclophane comprises a compound of Formula I

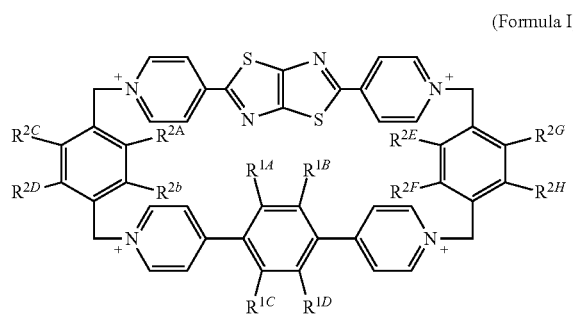

(Formula I)

wherein $R^{1A}$, $R^{1B}$, $R^{1C}$, $R^{1D}$, $R^{2A}$, $R^{2B}$, $R^{2C}$, $R^{2D}$, $R^{2E}$, $R^{2F}$, $R^{2G}$, and $R^{2H}$ are independently selected from the group consisting of hydrogen, a halogen, a $C_1$-$C_6$ alkyl, hydroxyl, a $C_1$-$C_6$ alkoxyl, amino, a $C_1$-$C_6$ alkylamine, a $C_3$-$C_7$ heterocyclyl, and phenyl.

11. The cyclophane of claim 10, wherein $R^{1A}$, $R^{1B}$, $R^{1C}$, $R^{1D}$, $R^{2A}$, $R^{2B}$, $R^{2C}$, $R^{2D}$, $R^{2E}$, $R^{2F}$, $R^{2G}$, and $R^{2H}$ are independently selected from the group consisting of hydrogen, the halogen, amino, a thiophene, and phenyl.

12. The cyclophane of claim 11 comprising a compound of Formula Ia

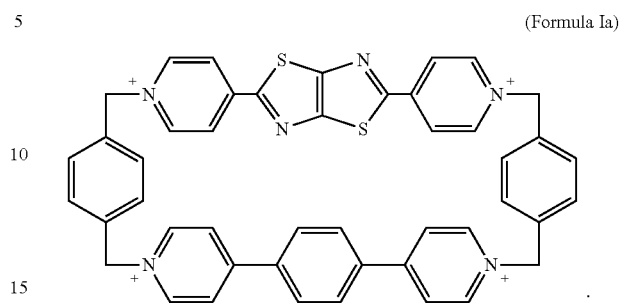

(Formula Ia)

13. A composition comprising the cyclophane of claim 1 further comprising a cytoplasmic delivery composition and/or a counterion.

14. A crystalline composition comprising the cyclophane of claim 1, wherein the composition is in the monoclinic space group $P2_1$.

15. A method for live-cell imaging, the method comprising incubating cells with the cyclophane of claim 1, stimulating the cyclophane with electromagnetic radiation, and detecting stimulated emission from the cyclophane.

16. The method of claim 15, wherein the cyclophane is simulated under live-cell conditions.

17. The method of claim 15, wherein the stimulated emission is detected for at least 5 seconds.

18. The method of claim 15, wherein cells incubated with up to 100 μM of the cyclophane for a period of 24 hours have a cell viability of at least 90% as measured by an MTT assay.

19. The method of claim 15, wherein the stimulated emission comprises fluorescence emission, wherein the stimulated emission is detected via fluorescence microscopy, wherein the stimulated emission is detected in the visible spectral region, or wherein the composition is stimulated by ultraviolet or visible radiation.

* * * * *